United States Patent
Bryan et al.

(10) Patent No.: US 11,434,250 B2
(45) Date of Patent: Sep. 6, 2022

(54) PYRAZOLO[1,5A]PYRIMIDINE DERIVATIVES AS IRAK4 MODULATORS

(71) Applicant: Genentech, Inc., South San Francisco, CA (US)

(72) Inventors: Marian C. Bryan, South San Francisco, CA (US); Joy Drobnick, South San Francisco, CA (US); James Richard Kiefer, Jr., South San Francisco, CA (US); Aleksandr Kolesnikov, South San Francisco, CA (US); Naomi S. Rajapaksa, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/863,741

(22) Filed: Apr. 30, 2020

(65) Prior Publication Data
US 2020/0262845 A1    Aug. 20, 2020

Related U.S. Application Data

(63) Continuation of application No. PCT/EP2017/077886, filed on Oct. 31, 2017.

(51) Int. Cl.
| | | |
|---|---|---|
| *C07D 519/00* | (2006.01) |
| *A61P 1/04* | (2006.01) |
| *A61P 11/00* | (2006.01) |
| *A61P 11/06* | (2006.01) |
| *A61P 13/12* | (2006.01) |
| *A61P 17/00* | (2006.01) |
| *A61P 17/06* | (2006.01) |
| *A61P 19/02* | (2006.01) |
| *A61P 19/06* | (2006.01) |
| *A61P 25/00* | (2006.01) |
| *A61P 25/04* | (2006.01) |
| *A61P 29/00* | (2006.01) |
| *A61P 35/00* | (2006.01) |
| *A61P 37/02* | (2006.01) |
| *A61P 37/06* | (2006.01) |
| *A61P 43/00* | (2006.01) |

(52) U.S. Cl.
CPC ................... *C07D 519/00* (2013.01)

(58) Field of Classification Search
CPC ........ C07D 519/00; A61P 43/00; A61P 37/06; A61P 37/02; A61P 35/00; A61P 29/00; A61P 25/04; A61P 25/00; A61P 19/06; A61P 19/02; A61P 17/06; A61P 17/00; A61P 13/12; A61P 11/06; A61P 11/00; A61P 1/04
See application file for complete search history.

(56) References Cited

U.S. PATENT DOCUMENTS

| | | |
|---|---|---|
| 2009/0163545 A1 | 6/2009 | Goldfarb |
| 2012/0015962 A1 | 1/2012 | Arora et al. |
| 2014/0163000 A1 | 6/2014 | Ahmad et al. |
| 2014/0200216 A1 | 7/2014 | Li et al. |

FOREIGN PATENT DOCUMENTS

| | | | |
|---|---|---|---|
| WO | 2005/058837 A1 | 6/2005 | |
| WO | 2012/007375 A1 | 1/2012 | |
| WO | 2012/07855 A1 | 6/2012 | |
| WO | WO-2014089379 A1 * | 6/2014 | ........... A61K 31/519 |
| WO | 2015/193846 A1 | 12/2015 | |
| WO | 2016/073895 A1 | 5/2016 | |
| WO | 2016/144844 A1 | 9/2016 | |
| WO | 2016/144846 A1 | 9/2016 | |
| WO | 2016/144848 A1 | 9/2016 | |
| WO | 2016/144849 A1 | 9/2016 | |
| WO | 2017/009798 A1 | 1/2017 | |
| WO | 2017/009806 A1 | 1/2017 | |
| WO | 2017/108723 A2 | 6/2017 | |

OTHER PUBLICATIONS

Seganish, W. M., "Inhibitors of interleukin-1 receptor-associated kinase 4 (IRAK4): a patent review (2012-2015)." Expert opinion on therapeutic patents 26.8 (2016): 917-932.*
Smith, G. F., "Identification of quinazoline based inhibitors of IRAK4 for the treatment of inflammation." Bioorganic & medicinal chemistry letters 27.12 (2017): 2721-2726.*
Koziczak-Holbro, M., "The critical role of kinase activity of interleukin-1 receptor-associated kinase 4 in animal models of joint inflammation." Arthritis & Rheumatism: Official Journal of the American College of Rheumatology 60.6 (2009): 1661-1671.*
Picard, C., "Pyogenic bacterial infections in humans with IRAK-4 deficiency." Science 299.5615 (2003): 2076-2079.*
Hynes Jr, J., "Advances in the discovery of small-molecule IRAK4 inhibitors." Annual reports in medicinal chemistry 49 (2014): 117-133.*
Kelly, P. N., "Selective interleukin-1 receptor-associated kinase 4 inhibitors for the treatment of autoimmune disorders and lymphoid malignancy." Journal of Experimental Medicine 212.13 (2015): 2189-2201.*
Verweij, M., "Medical-Ethical Dimensions of Preventive Medicine." Preventive Medicine between Obligation and Aspiration. Springer, Dordrecht, 2000. 25-49.*
CAS Registry Database, 1214608-12-4, (Compound with the Registry No. 1214608-12-4), pp. 1-3 Creation Date Mar. 25, 2010.
CAS Registry Database, 1258739-95-5, (Compound with the Registry No. 1258739-95-5), pp. 1 Creation Date Jan. 7, 2011.
CAS Registry Database, 1309337-74-3, (Compound with the Registry No. 1309337-74-3), pp. 1 Creation Date Jun. 14, 2011.
CAS Registry Database, 1311711-91-7, (Compound with the Registry No. 1311711-91-7), pp. 1-3 Creation Date Jul. 7, 2011.

(Continued)

*Primary Examiner* — John M Mauro
(74) *Attorney, Agent, or Firm* — Brian L. Buckwalter

(57) ABSTRACT

Compounds of Formula I and methods of use as Interleukin-1 Receptor Associated Kinase 4 (IRAK4) inhibitors are described herein.

20 Claims, 2 Drawing Sheets

(56) References Cited

OTHER PUBLICATIONS

CAS Registry Database, 1332092-83-7, (Compound with the Registry No. 1332092-83-7), pp. 1-3 Creation Date Sep. 14, 2011.
CAS Registry Database, 1332167-51-7, (Compound with the Registry No. 1332167-51-7), pp. 1 Creation Date Sep. 14, 2011.
CAS Registry Database, 1356058-08-6, (Compound with the Registry No. 1356058-08-6), pp. 1-3 Creation Date Feb. 8, 2012.
CAS Registry Database, 1575662-27-9, (Compounds with the Registry Nos. 1575662-127-9 and 1574985-62-8), pp. 1 Creation Date Mar. 28, 2014.
CAS Registry Database, 1582010-99-8, (Compound with the Registry No. 1582010-99-8), pp. 1-3 Creation Date Apr. 8, 2014.
CAS Registry Database, 1585340-91-5, (Compound with the Registry No. 1585340-91-5), pp. 1-3 Creation Date Apr. 16, 2014.
CAS Registry Database, 1829481-02-8, (Compounds with the Registry Nos. 1829481-02-8 and 1829481-01-7), pp. 1Creation Date Dec. 14, 2015.
CAS Registry Database, 1844896-04-3, (Compound with the Registry No. 1844896-04-3), pp. 1-4 Creation Date Jan. 11, 2016.
CAS Registry Database, 838811-58-8, (Compound with the Registry No. 838811-58-8), pp. 1 Creation Date Feb. 27, 2005.
Chaudhary, D., et al., "Recent Advances in the Discovery of Small Molecule Inhibitors of Interlekin-1 Receptor-Associated Kinase 4 (IRAK4) as a Therapeutic Target for Inflammation and Oncology Disorders" J Med Chem 58(1):96-110 (Jan. 8, 2015).
Goldfarb, D., et al., CAS Registry Database, 717829-94-2, 2009:846108 U.S. Appl. No. 12/341,615 entitled: "Method using lifespan-altering compounds for altering the lifespan of eukaryotic organisms, and screening for such compounds.", pp. 1-2Release Date Feb. 13, 2017.
"International Preliminary Report on Patentability—PCT/EP2017/077886" (Report dated May 7, 2019),:pp. 1-11 (dated May 16, 2019).
"International Search Report—PCT/EP2017/077886":pp. 1-8 (dated Jan. 19, 2018).
Lim, J., et al., "Discovery of 5-Amino-N-(1H-parazol-4yl)pyrazolo(1.5-a)pyrimidine-3carboxamide Inhibitors of IRAK4" ACS Med Chem Lett 6(6):683-688 (Jun. 11, 2015).

\* cited by examiner

PYRAZOLO[1,5A]PYRIMIDINE DERIVATIVES AS IRAK4 MODULATORS

CROSS-REFERENCE TO RELATED APPLICATION

This application is a continuation of International Application No. PCT/EP2017/077886 filed on Oct. 31, 2017, which claims the benefit under 35 U.S.C. 119(e) of U.S. Provisional Appl. No. 62/416,550, filed Nov. 2, 2016, and U.S. Provisional Appl. No. 62/417,893, filed Nov. 4, 2016, each of which is incorporated herein by reference in its entirety.

FIELD OF THE INVENTION

This invention pertains to compounds useful for inhibition of Interleukin-1 Receptor Associated Kinase 4 (IRAK4).

BACKGROUND OF THE INVENTION

TIR-domain (Toll-Interleukin 1 Receptor-domain) containing cell surface receptors such as the Toll-like receptors (TLR) and the IL-1 and IL-18 receptors play critical roles in innate immunity and have been implicated in the pathogenesis of autoimmunity. TLRs, for example, recognize pathogenic or endogenous ligands and provide a requisite signal for dendritic cell maturation and antigen presentation to T cell. Similarly, proteins that mediate signaling from these receptors have also been shown to play important roles in the pathogenesis of autoimmune disorders. For example mice deficient in MyD88, an adaptor protein that directly interacts with the TIR domain, are more susceptible to bacterial, fungal and parasitic infections. In addition, MyD88 deficient mice are resistant to experimental autoimmune encephalomyelitis (EAE) and streptococcal cell wall-induced arthritis.

The Interleukin-1 Receptor Associated Kinase (IRAK) family is comprised of four family members IRAK1, IRAK2, IRAK3 (also termed IRAK-M), and IRAK4. These proteins are characterized by a typical N-terminal death domain that mediates interaction with MyD88-family adaptor proteins and a centrally located kinase domain. Whereas IRAK1 and IRAK4 have kinase activity, IRAK2 and IRAK3 are catalytically inactive. Upon activation of their upstream cognate receptors, IRAK4 is thought to phosphorylate IRAK1, resulting in the activation and autophosphorylation of IRAK1 and subsequent phosphorylation of downstream substrates. The hyperphosphorylation of IRAK1 directs its dissociation from the receptor complex and its eventual ubiquitylation and proteasomal degradation. Phosphorylation of downstream substrates such as Pellino-2 ultimately leads to the activation of the MAPKs such as p38 and c-Jun N-terminal kinase (JNK) and NF-kB followed by production of pro-inflammatory cytokines, chemokines, and destructive enzyme.

The role of IRAK4 in innate immunity and in the pathogenesis of autoimmune diseases is emerging. See, e.g., Li et al., "IRAK-4: A novel member of the IRAK family with the properties of an IRAK-kinase," PNAS 2002, 99(8), 5567-5572; Flannery et al., "The interleukin-1 receptor-associated kinases: Critical regulators of innate immune signaling," Biochem Pharm 2010, 80(12), 1981-1991. Patients with destabilizing or null mutations in IRAK4 demonstrate defects in TLR signaling and the production of pro-inflammatory cytokines such as IL-1 and TNF as well as antiviral cytokines such as IFNα and IFNβ. These patients demonstrate an increased susceptibility to gram-positive bacterial infections although they are generally resistant to gram-negative bacterial, viral, and fungal infections. Similarly, IRAK4 deficient mice have defects in TLR- and IL-1-mediated cytokine production and exhibit an increased susceptibility to infection. IRAK1 deficient mice demonstrate a loss of responsiveness to lipopolysaccharides (LPS), IL-1, and IL-18 as well as impaired Th1 development. These mice were resistant to experimental autoimmune encephalomyelitis, exhibiting little or no CNS inflammation.

Accordingly, compounds that modulate the function of IRAK4 represent an attractive approach to the development of therapeutic agents for the treatment of diseases such as inflammatory, cell proliferative and immune-related conditions and diseases associated with IRAK-mediated signal transduction, such as rheumatoid arthritis, inflammatory bowel disease, multiple sclerosis, lupus, diabetes, obesity, allergic disease, psoriasis, asthma, graft rejection, cancer and sepsis.

SUMMARY OF THE INVENTION

One aspect of the invention includes a compound of Formula I

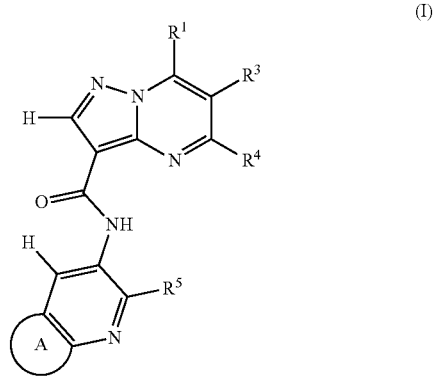

or a stereoisomer or pharmaceutically acceptable salt thereof, wherein:

$R^1$ is hydrogen or halo;

$R^3$ is hydrogen, halo, CN, OH, $C_{1-3}$alkyl, $C_{2-3}$alkenyl, $C_{3-7}$cycloalkyl, $C_1$-$C_3$alkanoyl, —($C_0$-$C_3$alkyl)C(O)NR$^6$R$^7$, —NR$^8$R$^9$, a 3-7 membered monocyclic saturated or partially saturated heterocyclic ring, a 5-6 membered monocyclic heteroaryl ring, or a 5-6 membered monocyclic aryl ring,
wherein any alkyl, alkanoyl, or alkenyl is independently optionally substituted by halo, oxo, CN, OH, $C_{1-3}$alkoxy, or $C_{1-3}$haloalkoxy, and
any cycloalkyl or other ring is independently optionally substituted by halo, oxo, CN, OH, $C_{1-3}$alkyl, or $C_{1-3}$haloalkyl;

$R^4$ is hydrogen, halo, $C_{1-3}$alkyl, $C_{2-3}$alkenyl, —($C_0$-$C_3$alkyl)C(O)R$^{13}$—($C_{0-3}$alkyl)C(O)NR$^{10}$R$^{11}$, or —NR$^8$R$^9$,
wherein any alkyl or alkenyl is independently optionally substituted by halo, oxo, CN, OH, $C_{1-3}$alkoxy, or $C_{1-3}$haloalkoxy;

$R^5$ is $C_{1-6}$alkyl, $C_{1-6}$alkoxy, $C_{3-10}$cycloalkyl, -a 3-11 membered saturated or partially saturated heterocyclic ring, or a 5-6 membered monocyclic heteroaryl ring, wherein any alkoxy is independently optionally substituted by halo, OH, $C_{3-7}$cycloalkyl, $C_{1-3}$alkoxy, or $C_{1-3}$haloalkoxy, and any cycloalkyl or other ring is optionally substituted by halo, oxo, CN, OH, $—(C_{0-3}alkyl)C(O)NR^{10}R^{11}$, or $C_{1-3}$alkyl optionally substituted by halo, oxo, CN, OH, or $—NR^8R^9$;

A is a 3-11 membered heterocyclic ring optionally substituted by halo, oxo, CN, OH, $C_{1-6}$alkyl, or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;

$R^6$ and $R^7$ are, independently at each occurrence, hydrogen, $C_{1-3}$alkyl, or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;

$R^8$, $R^9$, $R^{10}$ and $R^{11}$ are, independently at each occurrence, hydrogen, $C_{1-6}$alkyl, $C_{3-6}$cycloalkyl, a 3-11 membered saturated heterocyclic ring, $—C(O)R^{13}$, $—C(O)OR^{13}$, or $—C(O)NR^6R^7$, wherein any alkyl, cycloalkyl or other ring is independently optionally substituted by halo, oxo, CN, $C_{1-3}$alkyl, $C_{1-3}$haloalkyl, $C_{1-3}$alkoxy, $C_{1-3}$haloalkoxy, $—OR^{13}$, or $—NR^6R^7$;

$R^{12}$ is, independently at each occurrence, hydrogen, $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy; and $R^{13}$ is, independently at each occurrence, hydrogen, $C_{1-6}$alkyl, $C_{3-10}$cycloalkyl, or a 3-11 membered saturated heterocyclic ring, wherein any alkyl, cycloalkyl, or other ring is independently optionally substituted by halo, oxo, CN, OH, $C_{1-3}$alkyl, $C_{1-3}$haloalkyl, $C_{1-3}$alkoxy, $C_{1-3}$haloalkoxy, $—OR^{12}$, or $—NR^6R^7$.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease, an autoimmune disease or cancer.

Another aspect includes a method of preventing, treating or lessening the severity of a disease or condition responsive to the inhibition of IRAK4, in a patient. The method can comprise administering to the patient a therapeutically effective amount of a compound of the invention.

Another aspect includes the use of a compound of the invention in the manufacture of a medicament for the treatment of a disease responsive to the inhibition of IRAK4.

Another aspect includes a kit for treating a disease or disorder responsive to the inhibition of IRAK4. The kit can comprise a first pharmaceutical composition comprising a compound of the invention, and instructions for use.

DETAILED DESCRIPTION OF THE INVENTION

Definitions

Figure 1:
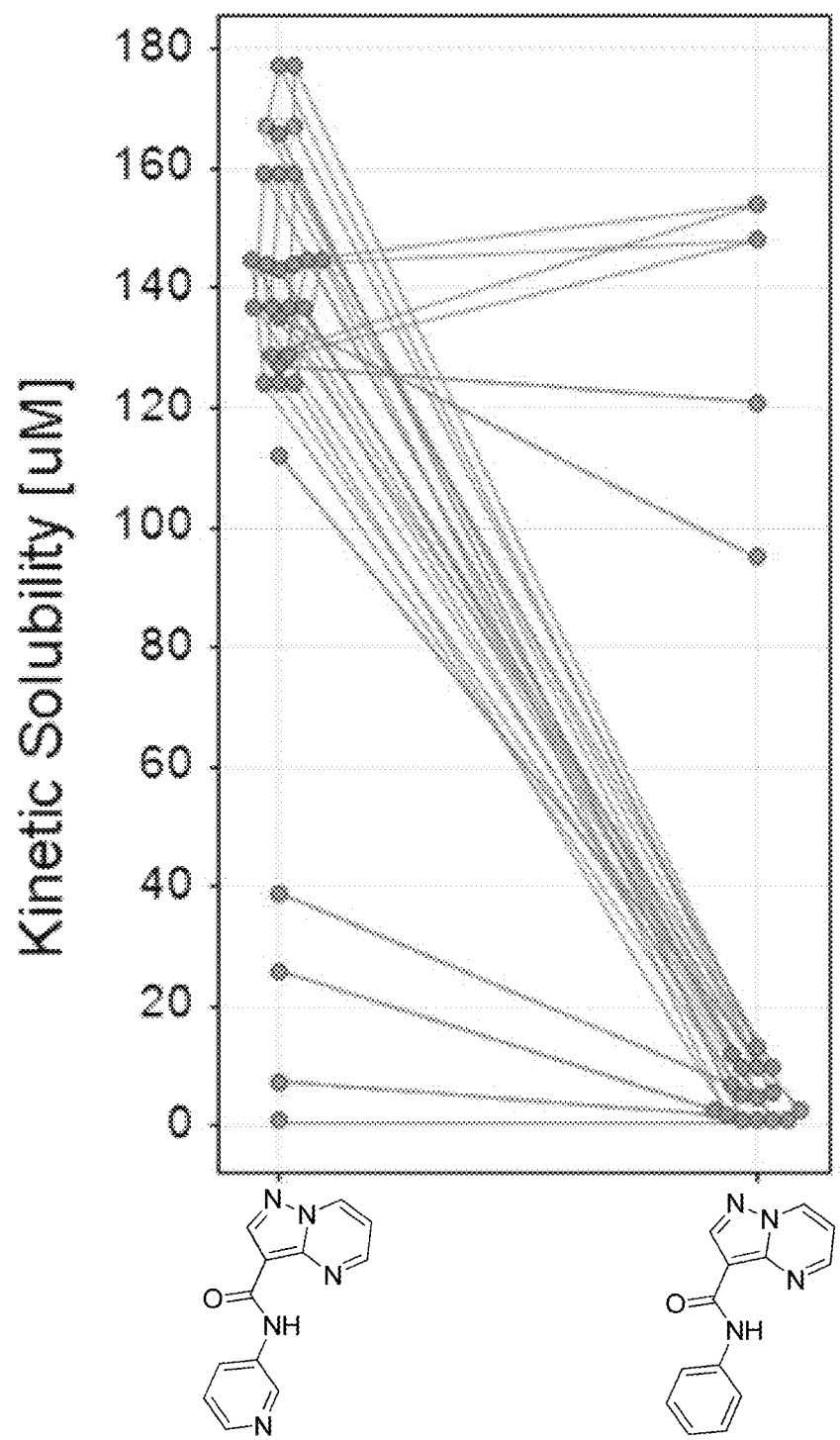
FIG. 1 illustrates a matched pair analysis regarding kinetic solubility values of certain compounds of the present invention having a particular substructure (points on the right) and corresponding compounds of a different substructure, wherein a single aromatic ring carbon (points on the right) is replaced with N (points on the left).

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula I and the compounds of Table 1 and Table 2 herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated, partially saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$ OH$^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy. "Haloalkoxy" refers to a haloalkyl group, as that term is defined herein, as R.

The term "alkanoyl" refers to group (alkyl)-C(=O)—, wherein alkyl is as defined herein. For example, $C_1$-$C_6$alkanoyl refers to a group of formula ($C_1$-$C_5$alkyl)-C(=O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line " ~ " that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$-$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4''-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1$-$C_6)$alkanoyloxymethyl, 1-(($C_1$-$C_6$)alkanoyloxy)ethyl, 1-methyl-1-(($C_1$-$C_6$)alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, alpha-amino$(C_1$-$C_4)$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{10}$-$C_6$) alkyl)$_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., IRAK4 activity) compared to normal.

In some embodiments, a compound of Formula I, such as a compound of Table 1 or Table 2, is selective for inhibition of IRAK4 over IRAK1. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of IRAK4 activity compared to IRAK1 activity, or is at least a 2-, 3-, 4-, 5-, 10-, 25-, 50-, 100-, 250-, or 500-fold better inhibitor of IRAK4 activity compared to IRAK1 activity.

A "therapeutically effective amount" means an amount of a compound of the present invention, such as a compound of Formula I (e.g., a compound of Table 1 or Table 2), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., lupus). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula I (e.g., a compound of Table 1 or Table 2), encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, lupus, chronic obstructive pulmonary disease (COPD), contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{33}P$, $^{35}S$, $^{18}F$, $^{36}Cl$, $^{123}I$, and $^{125}I$, respectively. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

IRAK4 Inhibitors

As noted, one aspect of the invention includes a compound of Formula I

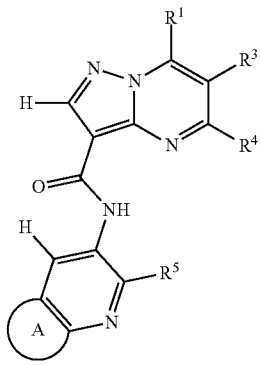

(I)

or a stereoisomer or pharmaceutically acceptable salt thereof,
wherein:
$R^1$ is hydrogen or halo;
$R^3$ is hydrogen, halo, CN, OH, $C_{1-3}$alkyl, $C_{2-3}$alkenyl, $C_{3-7}$cycloalkyl, $C_1$-$C_3$alkanoyl, —($C_0$-$C_3$alkyl)C(O)NR$^6$R$^7$, —NR$^8$R$^9$, a 3-7 membered monocyclic saturated or partially saturated heterocyclic ring, a 5-6 membered monocyclic heteroaryl ring, or a 5-6 membered monocyclic aryl ring,
  wherein any alkyl, alkanoyl, or alkenyl is independently optionally substituted by halo, oxo, CN, OH, $C_{1-3}$alkoxy, or $C_{1-3}$haloalkoxy, and
  any cycloalkyl or other ring is independently optionally substituted by halo, oxo, CN, OH, $C_{1-3}$alkyl, or $C_{1-3}$haloalkyl;
$R^4$ is hydrogen, halo, $C_{1-3}$alkyl, $C_{2-3}$alkenyl, —($C_0$-$C_3$alkyl)C(O)R$^{13}$ —($C_{0-3}$alkyl)C(O)NR$^{10R}$R$^{11}$, or —NR$^8$R$^9$,
  wherein any alkyl or alkenyl is independently optionally substituted by halo, oxo, CN, OH, $C_{1-3}$alkoxy, or $C_{1-3}$haloalkoxy;
$R^5$ is $C_{1-6}$alkyl, $C_{1-6}$alkoxy, $C_{3-10}$cycloalkyl, -a 3-11 membered saturated or partially saturated heterocyclic ring, or a 5-6 membered monocyclic heteroaryl ring,
  wherein any alkoxy is independently optionally substituted by halo, OH, $C_{3-7}$cycloalkyl, $C_{1-3}$alkoxy, or $C_{1-3}$haloalkoxy, and
  any cycloalkyl or other ring is optionally substituted by halo, oxo, CN, OH, —($C_{0-3}$alkyl)C(O)NR$^{10}$R$^{11}$, or $C_{1-3}$alkyl optionally substituted by halo, oxo, CN, OH, or —NR$^8$R$^9$;
A is a 3-11 membered heterocyclic ring optionally substituted by halo, oxo, CN, OH, $C_{1-6}$alkyl, or $C_{3-6}$cycloalkyl,
  wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
$R^6$ and $R^7$ are, independently at each occurrence, hydrogen, $C_{1-3}$alkyl, or $C_{3-6}$cycloalkyl,
  wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
$R^8$, $R^9$, $R^{10}$ and $R^{11}$ are, independently at each occurrence, hydrogen, $C_{1-6}$alkyl, $C_{3-6}$cycloalkyl, a 3-11 membered saturated heterocyclic ring, —C(O)R$^{13}$, —C(O)OR$^{13}$, or —C(O)NR$^6$R$^7$,
  wherein any alkyl, cycloalkyl or other ring is independently optionally substituted by halo, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;

R$^{12}$ is, independently at each occurrence, hydrogen, $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy; and R$^{13}$ is, independently at each occurrence, hydrogen, $C_{1-6}$alkyl, $C_{3-10}$cycloalkyl, or a 3-11 membered saturated heterocyclic ring, wherein any alkyl, cycloalkyl, or other ring is independently optionally substituted by halo, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$.

In some embodiments, a compound of Formula I is further defined as a compound of Formula (II):

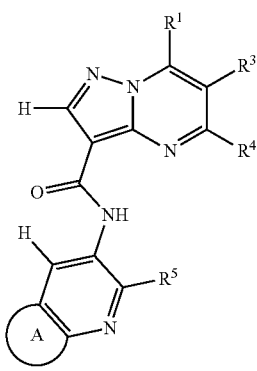

(II)

or a stereoisomer or pharmaceutically acceptable salt thereof,
wherein:

R$^1$ is hydrogen or halo;

R$^3$ is hydrogen, halo, CN, OH, $C_{1-3}$alkyl, $C_{2-3}$alkenyl, $C_{3-7}$cycloalkyl, $C_1$-$C_3$alkanoyl, ($C_0$-$C_3$alkyl)C(O)NR$^6$R$^7$, —NR$^8$R$^9$, a 3-7 membered monocyclic saturated or partially saturated heterocyclic ring, a 5-6 membered monocyclic heteroaryl ring, or a 5-6 membered monocyclic aryl ring, wherein any alkyl, alkanoyl, or alkenyl is independently optionally substituted by halo, oxo, CN, OH, $C_{1-3}$alkoxy, or $C_{1-3}$haloalkoxy, and any cycloalkyl or other ring is independently optionally substituted by halo, oxo, CN, OH, $C_{1-3}$alkyl, or $C_{1-3}$haloalkyl;

R$^4$ is hydrogen, halo, $C_{1-3}$alkyl, $C_{2-3}$alkenyl, —($C_{0-3}$alkyl)C(O)NR$^{10}$R$^{11}$, or —($C_0$-$C_3$alkyl)C(O)R$^{13}$, wherein any alkyl or alkenyl is independently optionally substituted by halo, oxo, CN, OH, $C_{1-3}$alkoxy, or $C_{1-3}$haloalkoxy;

R$^5$ is $C_{1-6}$alkyl, $C_{1-6}$alkoxy, $C_{3-10}$cycloalkyl, -a 3-11 membered saturated or partially saturated heterocyclic ring, or a 5-6 membered monocyclic heteroaryl ring, wherein any alkoxy is independently optionally substituted by halo, OH, $C_{3-7}$cycloalkyl, $C_{1-3}$alkoxy, or $C_{1-3}$haloalkoxy, and any cycloalkyl or other ring is optionally substituted by halo, oxo, CN, OH, —($C_{0-3}$alkyl)C(O)NR$^{10}$R$^{11}$, or $C_{1-3}$alkyl optionally substituted by halo, oxo, CN, OH, or —NR$^8$R$^9$;

A is a 3-11 membered heterocyclic ring optionally substituted by halo, oxo, CN, OH, $C_{1-6}$alkyl, or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;

R$^6$ and R$^7$ are, independently at each occurrence, hydrogen, $C_{1-3}$alkyl, or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;

R$^8$, R$^9$, R$^{10}$ and R$^{11}$ are, independently at each occurrence, hydrogen, $C_{1-6}$alkyl, $C_{3-6}$cycloalkyl, a 3-11 membered saturated heterocyclic ring, —C(O)R$^{13}$, —C(O)OR$^{13}$, or —C(O)NR$^6$R$^7$, wherein any alkyl, cycloalkyl or other ring is independently optionally substituted by halo, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;

R$^{12}$ is, independently at each occurrence, hydrogen, $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy; and R$^{13}$ is, independently at each occurrence, hydrogen, $C_{1-6}$alkyl, $C_{3-10}$cycloalkyl, or a 3-11 membered saturated heterocyclic ring, wherein any alkyl, cycloalkyl, or other ring is independently optionally substituted by halo, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$.

In some embodiments, R$^1$ and R$^4$ are each hydrogen, and R$^3$ is hydrogen, halo, CH$_3$, CH$_2$F, CHF$_2$, CF$_3$, cyclopropyl, or —C(O)CH$_3$. In some embodiments, R$^1$ and R$^4$ are each hydrogen, and R$^3$ is hydrogen or CH$_3$. In some embodiments, R$^1$, R$^3$ and R$^4$ are each hydrogen.

In some embodiments, R$^5$ is a 3-11 membered saturated or partially saturated heterocyclic ring optionally substituted by halo, oxo, CN, OH, —($C_{0-3}$alkyl)C(O)NR$^{10}$R$^{11}$, or $C_{1-3}$alkyl optionally substituted by halo, oxo, CN, OH, or —NR$^8$R$^9$. In some embodiments, R$^5$ is an N-linked 3-11 membered saturated heterocyclic ring optionally substituted by halo, oxo, CN, OH, —($C_{0-3}$alkyl)C(O)NR$^{10}$R$^{11}$, —OP(O)(OC$_{1-3}$alkyl)$_2$, or $C_{1-3}$alkyl optionally substituted by halo, oxo, CN, OH, or —NR$^8$R$^9$. In some embodiments, the ring heteroatoms of any 3-11 membered saturated or partially saturated heterocyclic ring of R$^5$ are selected from nitrogen and oxygen. In some embodiments, R$^5$ is N-linked piperidinyl, N-linked piperazinyl, or N-linked morpholinyl, wherein any R$^5$ is optionally substituted by halo, oxo, CN, OH, or $C_{1-3}$alkyl optionally substituted by halo, oxo, CN, or OH.

In some embodiments, the following portion of Formula I,

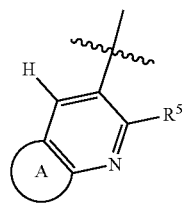

is further defined as I-A:

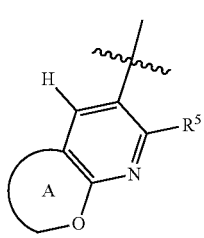
(I-A)

wherein A is a 5 or 6 membered ring optionally containing an additional ring heteroatom and wherein A is optionally substituted by halo, oxo, CN, OH, $C_{1-6}$alkyl, or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy. In some embodiments, I-A is further defined as I-B:

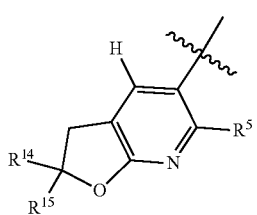
(I-B)

wherein $R^{14}$ and $R^{15}$ are each selected from halo, oxo, CN, OH, $C_{1-6}$alkyl, and $C_{3-6}$cycloalkyl,
wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
or $R^{14}$ and $R^{15}$ together form a $C_{3-6}$cycloalkyl or saturated or partially saturated 3-6 membered heterocyclic ring,
wherein any cycloalkyl or other ring is independently optionally substituted by halo, oxo, CN, OH, $C_{1-3}$alkyl, $C_{1-3}$haloalkyl, $C_{1-3}$alkoxy, or $C_{1-3}$haloalkoxy.

In some embodiments, $R^{14}$ and $R^{15}$ are each selected from halo, oxo, CN, OH, $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy.

In some embodiments, A is a 3-11 membered heterocyclic ring comprising only one oxygen as a ring atom and is optionally substituted by (i) OH or (ii) $C_{1-6}$alkyl optionally substituted by OH.

In some embodiments, the following portion of Formula I,

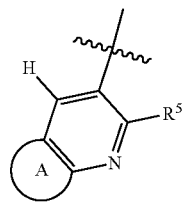

is further defined as I-C:

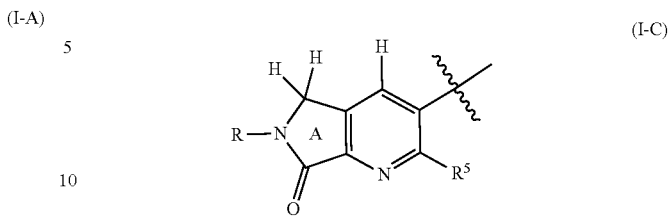
(I-C)

wherein the nitrogen of A is substituted by $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy.

In some embodiments, a compound of Formula I or II is not

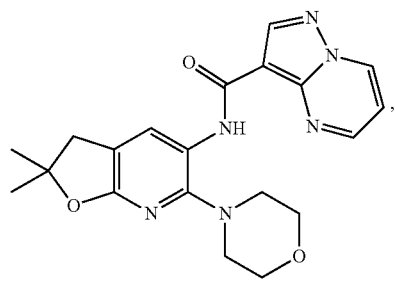
,

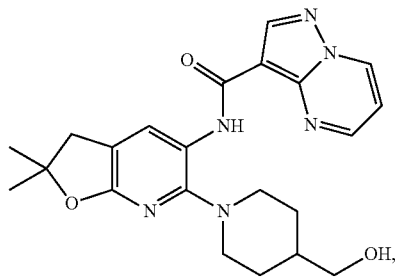
,

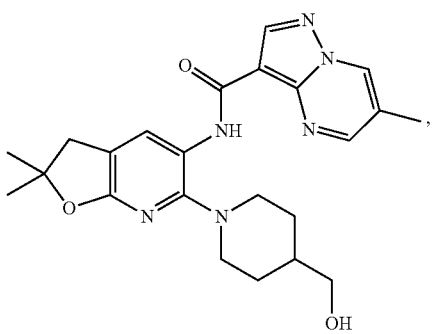
,

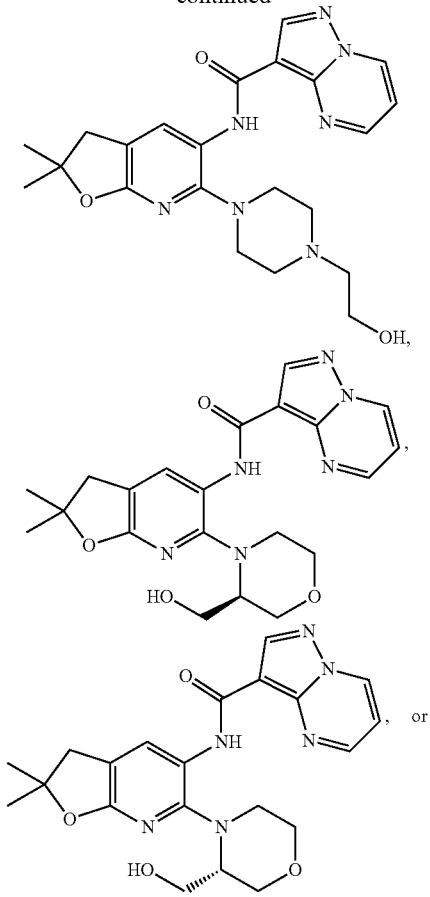

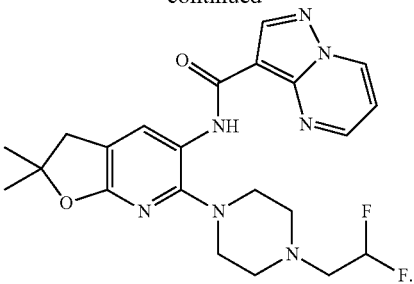

In some embodiments, the kinetic solubility of IRAK4 inhibitors described herein may be improved (that is, raised in value) and/or the plasma protein binding may be improved (that is, lowered in value) compared to matched pairs according to the following substructures:

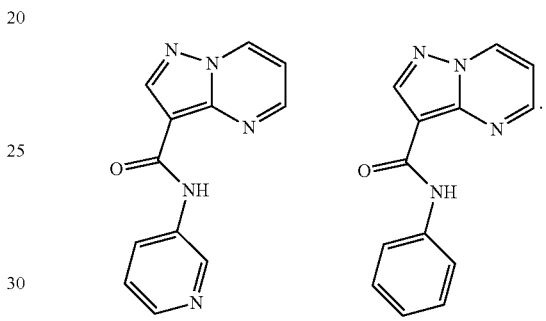

In some embodiments, a compound is selected from the group consisting of the compounds of Table 1 or Table 2, shown below, or a stereoisomer or pharmaceutically acceptable salt thereof.

TABLE 1

Exemplary compounds of the present invention. Salts of such compounds are also contemplated. See the Examples section for preparation of such compounds.

| Ex. | Structure | Name |
|---|---|---|
| 1 | 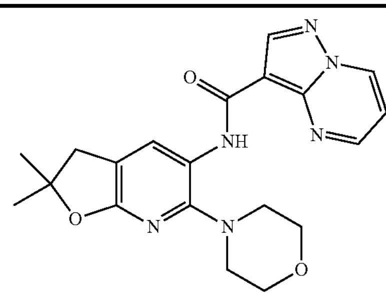 | N-(2,2-dimethyl-6-morpholino-3H-furo[2,3-b]pyridin-5-yl)pyrazolo[1,5-a]pyrimidine-3-carboxamide |
| 2 | 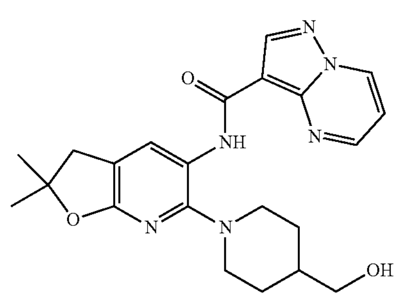 [SMILES: CC1(C)Cc2cc(NC(=O)c3cnn4cccnc34)c(N3CCC(CO)CC3)nc2O1] | N-[6-[4-(hydroxymethyl)-1-piperidyl]-2,2-dimethyl-3H-furo[2,3-b]pyridin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Ex. | Structure | Name |
|---|---|---|
| 3 | 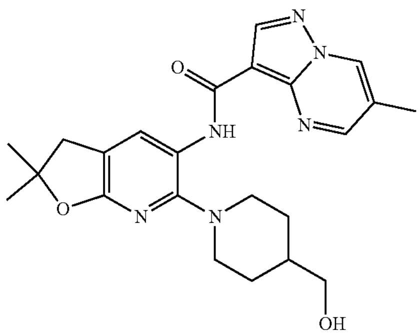 | N-[6-[4-(hydroxymethyl)-1-piperidyl]-2,2-dimethyl-3H-furo[2,3-b]pyridin-5-yl]-6-methyl-pyrazolo[1,5-a]pyrimidine-3-carboxamide |
| 4 | 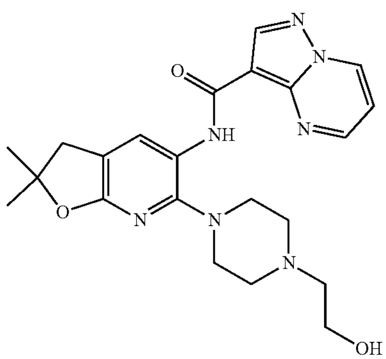 [SMILES: CC1(C)Cc2cc(NC(=O)c3cnn4cccnc34)c(N3CCN(CCO)CC3)nc2O1] | N-[6-[4-(2-hydroxyethyl)piperazin-1-yl]-2,2-dimethyl-3H-furo[2,3-b]pyridin-5-yl]pyrazolo[1,5-a]pyrimidine-3-carboxamide |
| 5 | 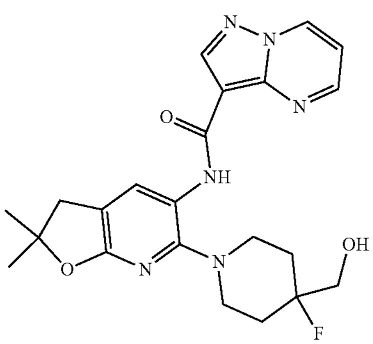 [SMILES: CC1(C)Cc2cc(NC(=O)c3cnn4cccnc34)c(N3CCC(F)(CO)CC3)nc2O1] | N-[6-[4-fluoro-4-(hydroxymethyl)-1-piperidyl]-2,2-dimethyl-3H-furo[2,3-b]pyridin-5-yl]pyrazolo[1,5-a]pyrimidine-3-carboxamide |
| 6 | 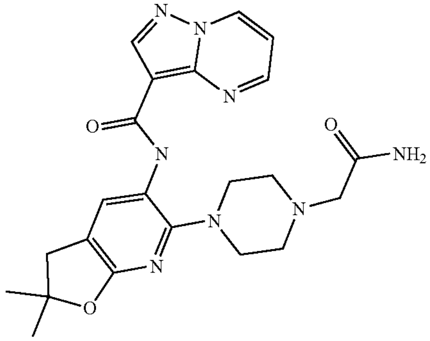 [SMILES: CC1(C)Cc2cc(NC(=O)c3cnn4cccnc34)c(N3CCN(CC(N)=O)CC3)nc2O1] | N-[6-[4-(2-amino-2-oxo-ethyl)piperazin-1-yl]-2,2-dimethyl-3H-furo[2,3-b]pyridin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Ex. | Structure | Name |
|---|---|---|
| 7&8 | 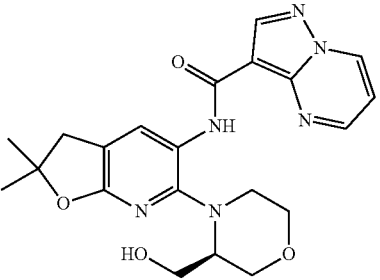 [SMILES: CC1(C)Cc2cc(NC(=O)c3cnn4cccnc34)c(N3CCOC[C@H]3CO)nc2O1] | N-[6-[(3R)-3-(hydroxymethyl)morpholin-4-yl]-2,2-dimethyl-3H-furo[2,3-b]pyridin-5-yl]pyrazolo[1,5-a]pyrimidine-3-carboxamide & N-[6-[(3S)-3-(hydroxymethyl)morpholin-4-yl]-2,2-dimethyl-3H-furo[2,3-b]pyridin-5-yl]pyrazolo[1,5-a]pyrimidine-3-carboxamide |
| 9 | 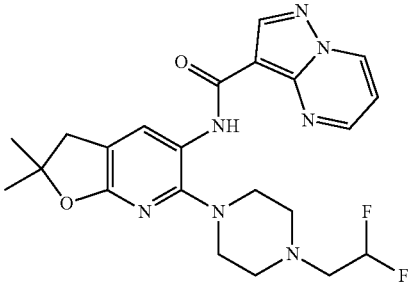 [SMILES: CC1(C)Cc2cc(NC(=O)c3cnn4cccnc34)c(N3CCN(CC(F)F)CC3)nc2O1] | N-[6-[4-(2,2-difluoroethyl)piperazin-1-yl]-2,2-dimethyl-3H-furo[2,3-b]pyridin-5-yl]pyrazolo[1,5-a]pyrimidine-3-carboxamide |
| 10&11 | 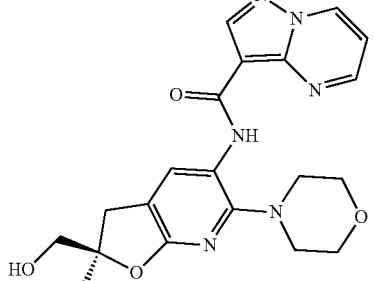 | N-[rac-(2S)-2-(hydroxymethyl)-2-methyl-6-morpholino-3H-furo[2,3-b]pyridin-5-yl]pyrazolo[1,5-a]pyrimidine-3-carboxamide & N-[rac-(2R)-2-(hydroxymethyl)-2-methyl-6-morpholino-3H-furo[2,3-b]pyridin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Ex. | Structure | Name |
|---|---|---|
| 12 | 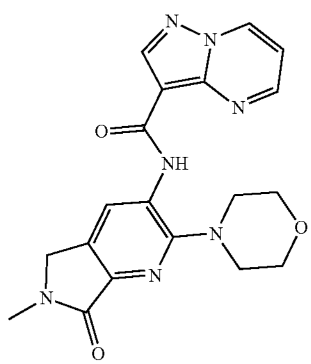 [SMILES: CN1Cc2cc(NC(=O)c3cnn4cccnc34)c(N3CCOCC3)nc2C1=O] | N-(6-methyl-2-morpholino-7-oxo-5H-pyrrolo[3,4-b]pyridin-3-yl)pyrazolo[1,5-a]pyrimidine-3-carboxamide |
| 13&14 | | N-[rac-(2S)-2-(1-hydroxy-1-methyl-ethyl)-2-methyl-6-morpholino-3H-furo[2,3-b]pyridin-5-yl]pyrazolo[1,5-a]pyrimidine-3-carboxamide & N-[rac-(2R)-2-(1-hydroxy-1-methyl-ethyl)-2-methyl-6-morpholino-3H-furo[2,3-b]pyridin-5-yl]pyrazolo[1,5-a]pyrimidine-3-carboxamide |

TABLE 1-continued

Exemplary compounds of the present invention. Salts of such compounds are also contemplated.
See the Examples section for preparation of such compounds.

| Ex. | Structure | Name |
|---|---|---|
| 15&16 | 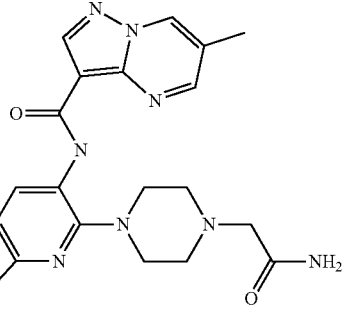 | 6-methyl-N-[rac-(2S)-6-[4-(2-amino-2-oxo-ethyl)piperazin-1-yl]-2-(hydroxymethyl)-2-methyl-3H-furo[2,3-b]pyridin-5-yl]pyrazolo[1,5-a]pyrimidine-3-carboxamide & 6-methyl-N-[rac-(2R)-6-[4-(2-amino-2-oxo-ethyl)piperazin-1-yl]-2-(hydroxymethyl)-2-methyl-3H-furo[2,3-b]pyridin-5-yl]pyrazolo[1,5-a]pyrimidine-3-carboxamide |
|  | 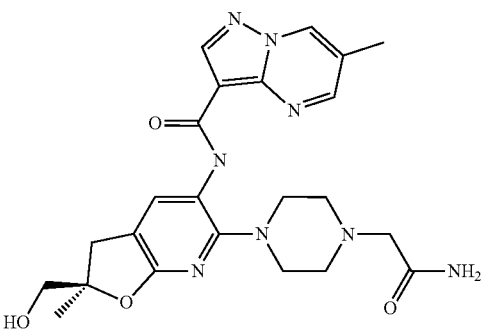 [SMILES: Cc1cnc2c(C(=O)Nc3cc4c(nc3N3CCN(CC(N)=O)CC3)O[C@@](C)(CO)C4)cnn2c1] |  |

TABLE 2

The following compounds can also be prepared utilizing methods described herein
in combination with the knowledge of those of skill in the art.

| Ex. | Structure | Name |
|---|---|---|
| 17 | 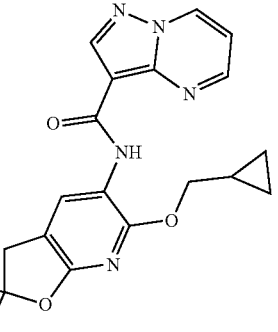 | N-[6-(cyclopropylmethoxy)-2,2-dimethyl-3H-furo[2,3-b]pyridin-5-yl]pyrazolo[1,5-a]pyrimidine-3-carboxamide |

TABLE 2-continued

The following compounds can also be prepared utilizing methods described herein in combination with the knowledge of those of skill in the art.

| Ex. | Structure | Name |
|---|---|---|
| 18 | 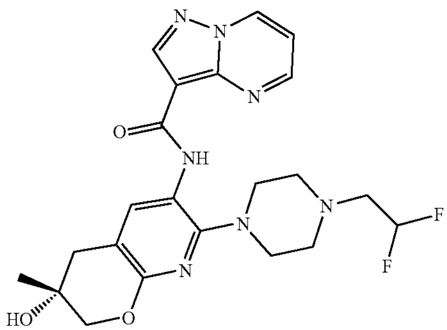 [SMILES: C[C@]1(O)COc2nc(N3CCN(CC(F)F)CC3)c(NC(=O)c3cnn4cccnc34)cc2C1] | N-[rac-(3R)-7-[4-(2,2-difluoroethyl)piperazin-1-yl]-3-hydroxy-3-methyl-2,4-dihydropyrano[2,3-b]pyridin-6-yl]pyrazolo[1,5-a]pyrimidine-3-carboxamide |
| 19 | 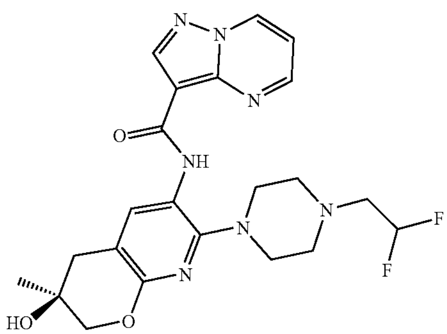 [SMILES: C[C@@]1(O)COc2nc(N3CCN(CC(F)F)CC3)c(NC(=O)c3cnn4cccnc34)cc2C1] | N-[rac-(3S)-7-[4-(2,2-difluoroethyl)piperazin-1-yl]-3-hydroxy-3-methyl-2,4-dihydropyrano[2,3-b]pyridin-6-yl]pyrazolo[1,5-a]pyrimidine-3-carboxamide |
| 20 | 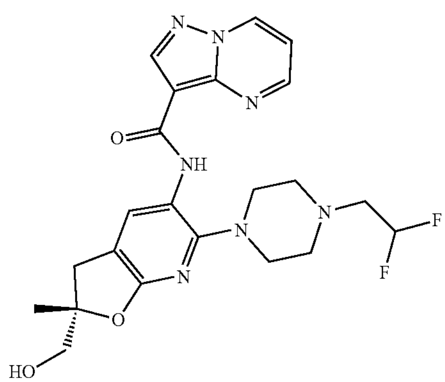 [SMILES: C[C@@]1(CO)Cc2cc(NC(=O)c3cnn4cccnc34)c(N3CCN(CC(F)F)CC3)nc2O1] | N-[rac-(2S)-6-[4-(2,2-difluoroethyl)piperazin-1-yl]-2-(hydroxymethyl)-2-methyl-3H-furo[2,3-b]pyridin-5-yl]pyrazolo[1,5-a]pyrimidine-3-carboxamide |
| 21 | 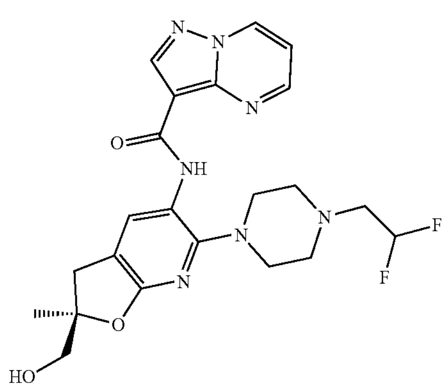 [SMILES: C[C@]1(CO)Cc2cc(NC(=O)c3cnn4cccnc34)c(N3CCN(CC(F)F)CC3)nc2O1] | N-[rac-(2R)-6-[-(2,2-difluoroethyl)piperazin-1-yl]-2-(hydroxymethyl)-2-methyl-3H-furo[2,3-b]pyridin-5-yl]pyrazolo[1,5-a]pyrimidine-3-carboxamide |

Synthesis of IRAK4 Inhibitors

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME I

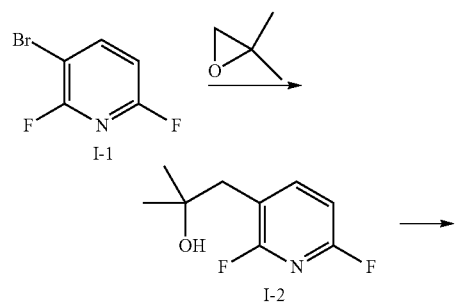

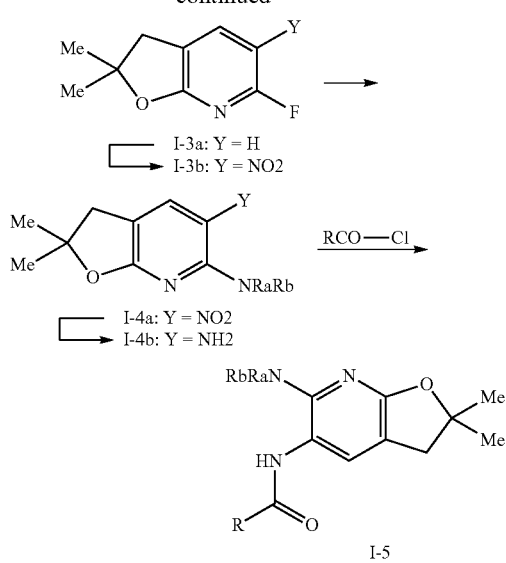

2,2-Dimethyl-2,3-dihydrofuro[2,3-b]pyridine-5,6-diamine derivatives exemplified herein can be prepared utilizing a 6-fluoro-2,2-dimethyl-5-nitro-2,3-dihydrofuro[2,3-b]pyridine I-3b as the key intermediate as depicted in Scheme II below. Addition of a 2,2-dimethyloxirane to 3-bromo-2,6-difluoropyridine in the presence of n-butyllithium affords the tertiary alcohol 1-2 which undergoes an intra-molecular cyclization to afford the I-3a. Nitration and displacement of the fluorine with an amine followed by reduction of the nitro and acylation with an acyl chloride is carried out in analogy with Scheme III below.

SCHEME II

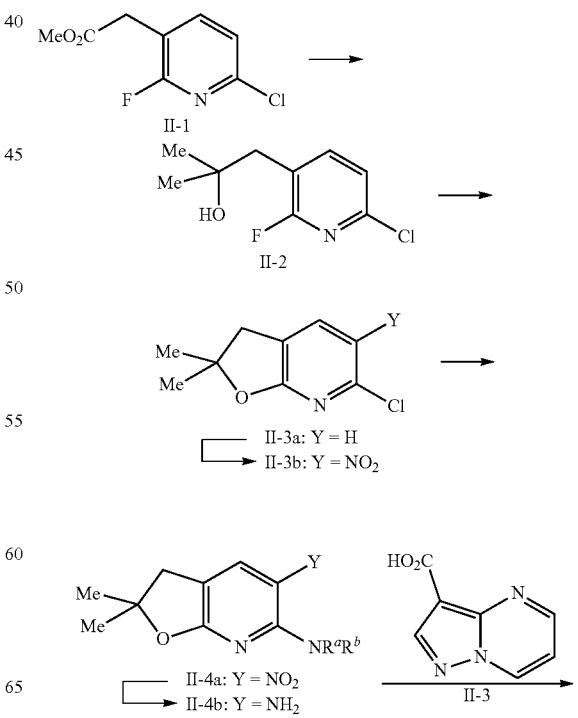

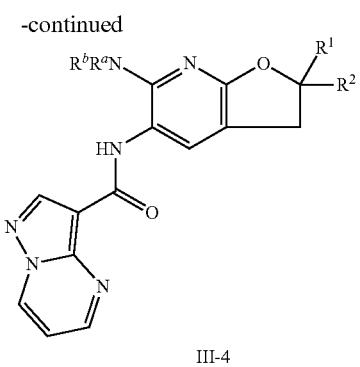

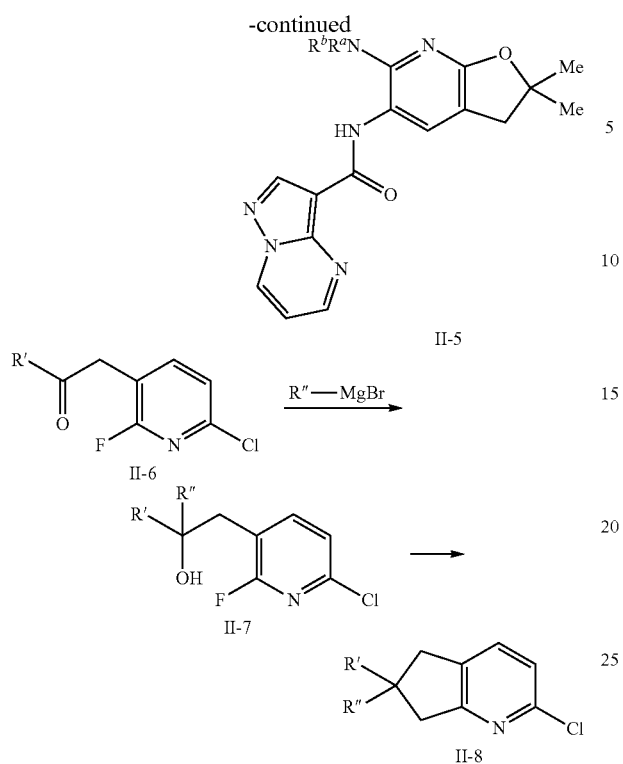

2,2-Dimethyl-2,3-dihydrofuro[2,3-b]pyridine-5,6-diamine exemplified herein can be prepared utilizing a 6-chloro-2,2-dimethyl-5-nitro-2,3-dihydrofuro[2,3-b]pyridine II-3b as the key intermediate as depicted in Scheme II. Addition of a methyl Grignard to methyl 2-(6-chloro-2-fluoropyridin-3-yl)acetate affords the tertiary alcohol II-2 which undergoes an intra-molecular cyclization to afford II-3a. Nitration and displacement of the chloride with an amine followed by reduction of the nitro and acylation with I-3 is carried out in analogy with Scheme III below. One skilled in the art will appreciate that the corresponding 5-fluoro and 5-bromo derivatives are readily available from methyl 2-(2,5-difluoropyridin-3-yl)acetate and methyl 2-(5-bromo-2-fluoropyridin-3-yl)acetate, respectively.

SCHEME III

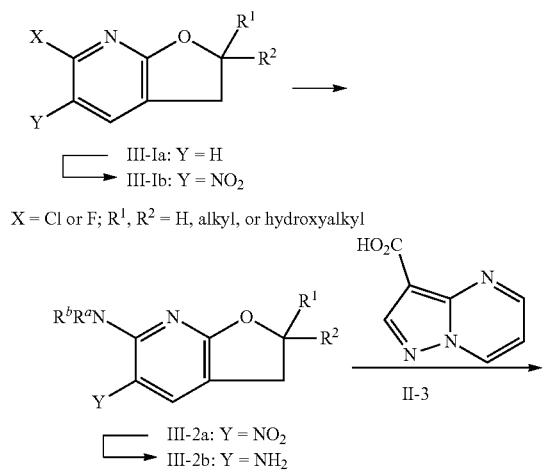

Regarding Scheme III, requisite 2,3-dihydrofuro[2,3-b]pyridinyl derivatives can be prepared by nitration of 6-halo-2,3-dihydrofuro[2,3-b]pyridine derivatives III-1a to afford III-1b followed by displacement of the halogen with an amine to afford III-2a. Typical amines include morpholine and 3-hydroxymethyl piperidine. Reduction of the nitro group and condensation with pyrazolo[1,5-a]pyrimidine-3-carboxylic acid (I-3), or an activated derivative thereof, affords the desired amides. The requisite precursors are commercially available or are prepared as described herein.

Aromatic nitration is well known and can be conducted under a variety of conditions known in the art. Nitration can be carried out, for example, by exposing an aromatic compound to concentrated nitric acid and sulfuric acid. Active substrates can be nitrated with $HNO_3$ alone or in $H_2O$, HOAc and acetic anhydride and active compounds may be oxidized by mixtures of $HNO_3$ and $H_2SO_4$. Other nitrating reagents include $NaNO_3$/TFA, $Cu(NO_3)_2$/HOAc/$Ac_2O$, $N_2O_4$, $NO_2^+BF_4^-$, $NO_2^+PF6^-$ and $NO_2^+CF_3SO^{4-}$. See, e.g., J. March, *Advanced Organic Chemistry*, John Wiley & Sons: New York, N.Y., 1992, pp. 522-23.

Reduction of the nitro group can be carried out with a variety of well-known reducing agents. For example, the nitro can be reduced under a hydrogen atmosphere in the presence of an inert solvent and in the presence of a metal effective to catalyze hydrogenation reactions such as platinum or palladium. The reduction can also be carried out with an activated metal such as activated iron, zinc or tin (produced for example by washing iron powder with a dilute acid solution such as dilute hydrochloric acid).

Coupling of the amine III-2b intermediate with II-3 is achieved with commonly used coupling reagents or, alternatively, 3 can be converted to the corresponding acid chloride and condensed with III-2b.

Acylation of a primary amine with an acid chloride is typically carried out in an inert solvent such as DMF, DCM, THF, pyridine with or without water as a co-solvent, at temperatures between 0° C. and 60° C. generally in the presence of a base such as $Na_2CO_3$, $NaHCO_3$, $K_2CO_3$, DIPEA, TEA or pyridine and the like to afford the corresponding amide. Carboxylic acids can be converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine.

Alternatively a carboxylic acid can be converted in situ into activated derivatives by utilizing reagents developed for peptide synthesis which are well known to those skilled in the art. These activated acids were reacted directly with the amines as described to afford the corresponding amide. Common coupling reagents include EDC, DCC, benzotriazol-1-yloxy-tris(dimethylamino)-phosphonium hexafluorophosphate (BOP), bromo-tris-pyrrolidinophosphonium hexafluorophosphate (PyBrOP), 2-fluoro-1-methylpyridinium p-toluenesulphonate (Mukaiyama's reagent), O-(7-azabenzotriazol-1-yl)-N,N,N',N'-tetramethyluronium hexafluorophosphate (HATU), 1-hydroxy-7-azabenzotriazole (HOAt) or (3-hydroxy-3H-1,2,3-triazolo[4,5-b]pyridinato-O)tri-1-pyrrolidinylphosphonium hexafluorophosphate (PyAOP) optionally in the presence of modifiers such as HOBt, with or without a base such NMM, TEA or DIPEA in an inert solvent such as DMF or DCM at temperatures between 0° C. and 60° C. Acylation of amines (see, e.g., J. March, supra pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411; R. C. Larock, *Comprehensive Organic Transformations—A Guide to Functional Group Preparations*, 1989, VCH Publishers Inc., New York; pp. 972-976) has been reviewed.

Methods of Treatment with and Uses of IRAK 4 Inhibitors

Compounds of the present invention are useful as IRAK4 inhibitors. Accordingly, in one embodiment is provided a method of contacting a cell, such as an ex vivo cell, with a compound of the present invention to inhibit IRAK4 activity in the cell.

Also provided is a pharmaceutical composition comprising a compound of Formula I, or a stereoisomer or pharmaceutically acceptable salt thereof, and a pharmaceutically acceptable excipient, carrier or diluent. Compounds of the invention, including pharmaceutical compositions comprising such compounds, may be used in the methods described herein.

Further provided is a method of preventing, treating, or lessening the severity of a disease or condition responsive to the inhibition of IRAK4 in a patient, comprising administering to the patient a therapeutically effective amount of a compound of the present invention, or a stereoisomer or pharmaceutically acceptable salt thereof.

Also provided is a method for treating cancer in a patient, comprising administering to the patient a therapeutically effective amount of a compound of the present invention, or a stereoisomer or pharmaceutically acceptable salt thereof.

Further provided is a method for treating an inflammatory or autoimmune disease in a patient, comprising administering to the patient a therapeutically effective amount of a compound of the present invention, or a stereoisomer or pharmaceutically acceptable salt thereof. In some embodiments, the disease is selected from the group consisting of Crohn's disease, ulcerative colitis, Irritable Bowel Disorder (IBD), asthma, graft versus host disease, allograft rejection, chronic obstructive pulmonary disease (COPD), rheumatoid arthritis, systemic lupus erythematosus, lupus nephritis, cutaneous lupus, psoriasis, systemic onset juvenile idiopathic arthritis, multiple sclerosis, neuropathic pain, gout, and gouty arthritis.

In some embodiments, other diseases and conditions responsive to the inhibition of IRAK4 that can be treated using a compound of the present invention include metabolic syndromes, atherosclerosis, and neurodegeneration.

Further provided is the use of a compound of the present invention, or a stereoisomer or pharmaceutically acceptable salt thereof, in therapy. In some embodiments, use of a compound of the present invention, or a stereoisomer or pharmaceutically acceptable salt thereof, is provided in the treatment of an inflammatory disease. In some embodiments, use of a compound of the present invention, or a stereoisomer or pharmaceutically acceptable salt thereof, is provided for the preparation of a medicament for the treatment of an inflammatory disease. Furthermore, in some embodiments, a compound of the present invention, or a stereoisomer or pharmaceutically acceptable salt thereof, is provided for use in the treatment of an inflammatory disease.

Also provided is a method of inhibiting IRAK4 in a patient in need of therapy, comprising administering to the patient a compound of the present invention.

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I, or a stereoisomer or pharmaceutically acceptable salt thereof, with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IRAK4 activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, or a stereoisomer or pharmaceutically acceptable salt thereof, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

A dose to treat human patients may range from about 0.1 mg to about 1000 mg of a compound of Formula I, or a stereoisomer or pharmaceutically acceptable salt thereof. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, or a stereoisomer or pharmaceutically acceptable salt thereof. A further embodiment includes a pharmaceutical composition comprising a compound of Formula I, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein. The second compound of the pharmaceutical combination formulation or dosing regimen preferably has complementary activities to the compound of Formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of at least one compound of Formula I, or a stereoisomer or pharmaceutically acceptable salt thereof, and the use of at least one other treatment method. The amounts of the compound(s) of Formula I and the other pharmaceutically active agent(s) and the relative timings of administration will be selected in order to achieve the desired combined therapeutic effect.

43

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of Formula I, such as tablets or capsules. Such a kit can include a number of unit dosages. An example of such a kit is a "blister pack". Blister packs are well known in the packaging industry and are widely used for packaging pharmaceutical unit dosage forms.

EXAMPLES

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-(2,2-dimethyl-6-morpholino-2,3-dihydrofuro[2,3-b]pyridin-5-yl)pyrazolo[1,5-a]pyrimidine-3-carboxamide

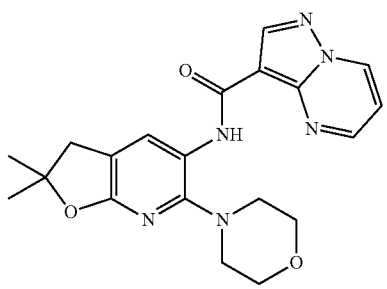 [SMILES: CC1(C)Cc2cc(NC(=O)c3cnn4cccnc34)c(N3CCOCC3)nc2O1]

Step A. 1-(2,6-Difluoro-3-pyridyl)-2-methyl-propan-2-ol

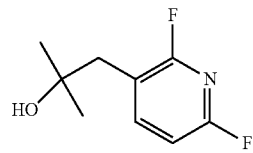

To the solution of 3-bromo-2,6-difluoro-pyridine (5.22 g, 25.57 mmol) in tetrahydrofuran (20 mL) at −78° C. under nitrogen was added dropwise n-butyllithium (2.5M, 11 mL, 28 mmol). The reaction was maintained at −78° C. for 30 min followed by addition of 2,2-dimethyloxirane (2.7 ml, 30.7 mmol) and boron trifluoride diethyl etherate (3.9 ml, 30.7 mmol). After 2 h at −78° C., the reaction was allowed to rt, quenched with water (200 ml) and extracted with dichloromethane (20 ml*3). The organic phases were combined, concentrated and the residue was purified by silica gel chromatography (eluting gradient 0-30% isopropyl acetate:heptanes) to afford the desired product as a yellow oil (1630 mg, 34% yield). MS (ESI): m/z=188.1 [M+1]$^+$.

Step B. 6-Fluoro-2,2-dimethyl-3H-furo[2,3-b]pyridine

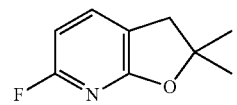

A mixture of potassium tert-butoxide (300 mg, 2.67 mmol) and 1-(2,6-difluoro-3-pyridyl)-2-methyl-propan-2-ol (200 mg, 1.07 mmol) in tetrahydrofuran (6 ml) was stirred at 20° C. for 2 h. The reaction mixture was diluted with ethyl acetate (20 ml), washed with water (20 ml×3), dried over anhydrous sodium sulfate, and concentrated in vacuo. The residue was purified by silica gel chromatography (eluting gradient 0-80% petroleum ether:ethyl acetate) to afford the desired product as a colorless oil (105 mg, 54% yield). MS (ESI): m/z=168.1 [M+H]$^+$.

Step C. 6-Fluoro-2,2-dimethyl-5-nitro-3H-furo[2,3-b]pyridine

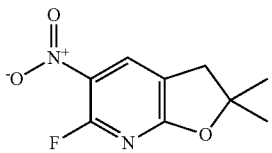

To a solution of 6-fluoro-2,2-dimethyl-3H-furo[2,3-b]pyridine (210 mg, 1.26 mmol) in acetic acid (3 mL) and acetic anhydride (3 mL) was added copper (II) nitrate (705.6 mg, 3.76 mmol) at 0° C. and the resulting mixture was stirred at 20° C. for 48 h. The reaction was diluted with water and extracted with ethyl acetate (10 mL). The combined organic phases were washed with saturated sodium bicarbonate solution and brine, dried over anhydrous sodium sulfate, and concentrated in vacuo to afford the desired product as a white solid (290 mg, 93% yield). MS (ESI): m/z=213.0 [M+H]⁺.

Step D. 2,2-dimethyl-6-morpholino-5-nitro-2,3-dihydrofuro[2,3-b]pyridine

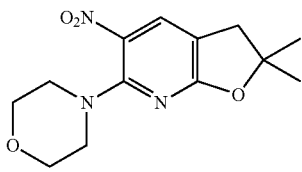 [SMILES: CC1(C)Cc2cc(N)c(N3CCOCC3)nc2O1]

A mixture of 6-fluoro-2,2-dimethyl-5-nitro-3H-furo[2,3-b]pyridine (Intermediate 5, 164 mg, 0.77 mmol) and morpholine (1 mL) in acetonitrile (2 mL) was stirred at ambient temperature for 2 h. The mixture was concentrated in vacuo and the yellow residue partitioned between 1% aqueous citric acid and ethyl acetate. The organic phase was isolated and washed with water and brine, dried over magnesium sulfate and concentrated. The yellow residue was purified by silica gel chromatography (eluting gradient 0-30% isopropyl acetate:heptanes) to afford 2,2-dimethyl-6-morpholino-5-nitro-2,3-dihydrofuro[2,3-b]pyridine (105 mg, 49% yield). MS (ESI): m/z=280 [M+1]⁺.

Step E. 2,2-dimethyl-6-morpholino-2,3-dihydrofuro[2,3-b]pyridin-5-amine

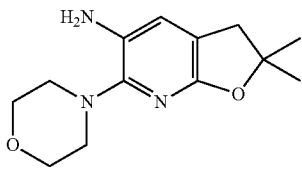

A solution of 2,2-dimethyl-6-morpholino-5-nitro-3H-furo[2,3-b]pyridine (105 mg, 0.38 mmol) in dioxane was hydrogenated at 1 atm over 10% palladium on carbon (50 mg) for 3 h. The mixture was filtered through celite and the filtrate concentrated to afford 2,2-dimethyl-6-morpholino-2,3-dihydrofuro[2,3-b]pyridin-5-amine (91 mg, 96% yield) which was used without further purification. MS (ESI): m/z=250 [M+1]⁺.

Step F. N-(2,2-dimethyl-6-morpholino-2,3-dihydrofuro[2,3-b]pyridin-5-yl)pyrazolo[1,5-a]pyrimidine-3-carboxamide

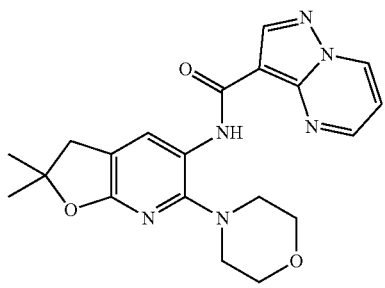 [SMILES: CC1(C)Cc2cc(NC(=O)c3cnn4cccnc34)c(N3CCOCC3)nc2O1]

A mixture of 2,2-dimethyl-6-morpholino-3H-furo[2,3-b]pyridin-5-amine (90 mg, 0.36 mmol), pyrazolo[1,5-a]pyrimidine-3-carbonyl chloride hydrochloride (94 mg, 0.43 mmol), 4-dimethylaminopyridine (9 mg, 0.072 mmol) and N,N-diisopropylethylamine (0.132 ml, 0.72 mmol) was subjected to microwave heating at 110° C. for 30 min. The mixture was concentrated and the residue partitioned between ethyl acetate and water. The organic phase was isolated, washed with 5% aqueous citric acid, saturated aqueous sodium bicarbonate, water and brine, dried over magnesium sulfate and concentrated. The residue was purified by silica gel chromatography (eluting gradient 0-70% isopropyl acetate:heptanes) to afford N-(2,2-dimethyl-6-morpholino-2,3-dihydrofuro[2,3-b]pyridin-5-yl)pyrazolo[1,5-a]pyrimidine-3-carboxamide (89 mg, 63% yield). ¹H NMR (400 MHz, DMSO-d₆) δ 10.07 (s, 1H), 9.38 (dd, J=7.0, 1.6 Hz, 1H), 8.97 (dd, J=4.2, 1.7 Hz, 1H), 8.70 (s, 1H), 8.54 (d, J=1.2 Hz, 1H), 7.35 (dd, J=7.0, 4.2 Hz, 1H), 3.87-3.76 (m, 4H), 3.04 (d, J=1.2 Hz, 2H), 3.00-2.89 (m, 4H), 1.44 (s, 6H). MS (ESI): m/z=395 [M+1]⁺.

Example 2

N-(6-(4-(Hydroxymethyl)piperidin-1-yl)-2,2-dimethyl-2,3-dihydrofuro[2,3-b]pyridin-5-yl)pyrazolo[1,5-a]pyrimidine-3-carboxamide

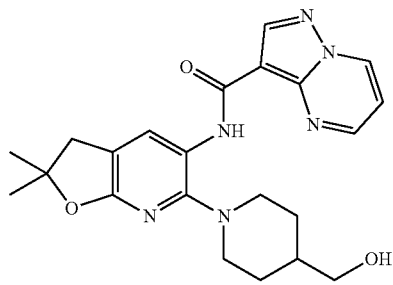 [SMILES: CC1(C)Cc2cc(NC(=O)c3cnn4cccnc34)c(N3CCC(CO)CC3)nc2O1]

Step A. (1-(2,2-Dimethyl-5-nitro-2,3-dihydrofuro[2,3-b]pyridin-6-yl)piperidin-4-yl)methanol

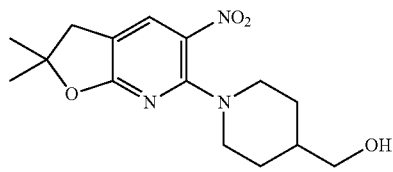

A mixture of 6-fluoro-2,2-dimethyl-5-nitro-3H-furo[2,3-b]pyridine (Example 1, Step C; 380 mg, 0.77 mmol), 4-piperidylmethanol (413 mg, 2.0 mmol) and N,N-diisopropylethylamine (0.63 ml, 3.58 mmol) in acetonitrile (2 mL) was stirred at 50° C. for 2 h. The mixture was partitioned between 1% aqueous citric acid and ethyl acetate. The organic phase was isolated and washed with water and brine, dried over magnesium sulfate and concentrated. The yellow residue was purified by silica gel chromatography (eluting gradient 0-50% isopropyl acetate:heptanes) to afford (1-(2,2-dimethyl-5-nitro-2,3-dihydrofuro[2,3-b]pyridin-6-yl)piperidin-4-yl)methanol (388 mg, 71% yield) as a yellow foam. MS (ESI): m/z=308 [M+1]⁺.

Step B. [1-(5-Amino-2,2-dimethyl-3H-furo[2,3-b]pyridin-6-yl)-4-piperidyl]methanol

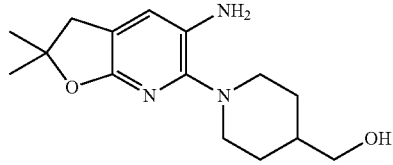 [SMILES: CC1(C)Cc2cc([N+](=O)[O-])c(N3CCC(CO)CC3)nc2O1]

[1-(5-Amino-2,2-dimethyl-3H-furo[2,3-b]pyridin-6-yl)-4-piperidyl]methanol was made in a manner analogous to Example 1, Step E to give the desired product (180 mg, quant.) which was used without further purification. MS (ESI): m/z=278 [M+1]$^+$.

Step C. N-(6-(4-(Hydroxymethyl)piperidin-1-yl)-2,2-dimethyl-2,3-dihydrofuro[2,3-b]pyridin-5-yl)pyrazolo[1,5-a]pyrimidine-3-carboxamide

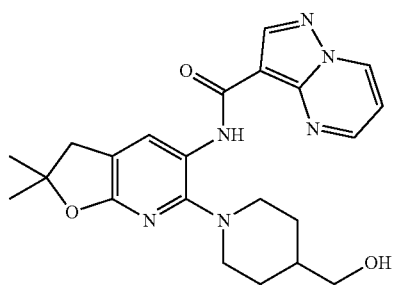 [SMILES: CC1(C)Cc2cc(NC(=O)c3cnn4cccnc34)c(N3CCC(CO)CC3)nc2O1]

The title compound was made in a manner analogous to Example 1, Step F to give N-(6-(4-(hydroxymethyl)piperidin-1-yl)-2,2-dimethyl-2,3-dihydrofuro[2,3-b]pyridin-5-yl)pyrazolo[1,5-a]pyrimidine-3-carboxamide (99 mg, 36% yield). $^1$H NMR (400 MHz, DMSO-d$_6$) δ 10.15 (s, 1H), 9.38 (dd, J=7.0, 1.6 Hz, 1H), 8.90 (dd, J=4.2, 1.7 Hz, 1H), 8.70 (s, 1H), 8.60-8.54 (m, 1H), 7.35 (dd, J=7.0, 4.2 Hz, 1H), 4.52 (t, J=5.3 Hz, 1H), 3.41 3.35 (m, 2H), 3.11 (d, J=11.7 Hz, 2H), 3.03 (d, J=1.2 Hz, 2H), 2.70 (t, J=11.2 Hz, 2H), 1.72 (d, J=10.1 Hz, 2H), 1.56-1.48 (m, 3H), 1.43 (s, 6H). MS (ESI): m/z=423 [M+1]$^+$.

Example 3

N-(6-(4-(Hydroxymethyl)piperidin-1-yl)-2,2-dimethyl-2,3-dihydrofuro[2,3-b]pyridin-5-yl)-6-methylpyrazolo[1,5-a]pyrimidine-3-carboxamide

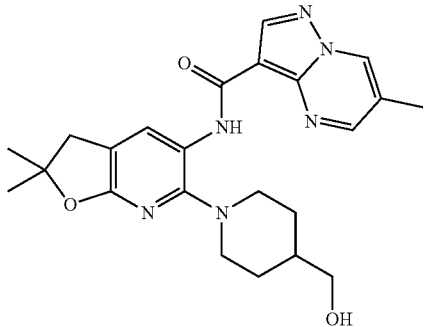

Step A. 6-Methylpyrazolo[1,5-a]pyrimidine-3-carbonyl chloride

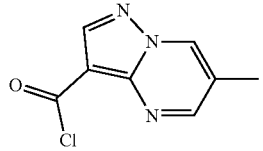

A mixture of 6-methylpyrazolo[1,5-A]pyrimidine-3-carboxylic acid (US201215962, Preparation 48; 150.0 mg, 0.8500 mmol), thionyl chloride (6 mL, 0.85 mmol) and N,N-dimethylformamide (0.01 mL, 0.85 mmol) was stirred at 80° C. for 2 h. The reaction was concentrated under reduced pressure and taken on without further purification.

Step B. N-(6-(4-(Hydroxymethyl)piperidin-1-yl)-2,2-dimethyl-2,3-dihydrofuro[2,3-b]pyridin-5-yl)-6-methylpyrazolo[1,5-a]pyrimidine-3-carboxamide

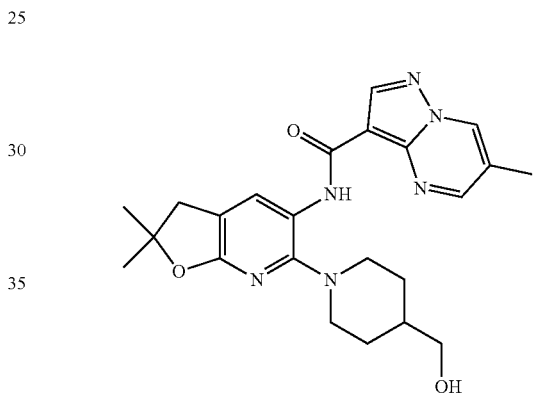

To N,N-diisopropylethylamine (163.87 mg, 1.62 mmol) and [1-(5-amino-2,2-dimethyl-3H-furo[2,3-b]pyridin-6-yl)-4-piperidyl]methanol (Example 2, Step B; 150.0 mg, 0.540 mmol) in dichloromethane (6 mL) was added 6-methylpyrazolo[1,5-a]pyrimidine-3-carbonyl chloride (158.7 mg, 0.81 mmol) and the mixture was stirred at 15° C. for 12 h. The mixture was concentrated, resuspended in methanol (15 mL) and 1M sodium hydroxide (2 mL) and stirred at 15° C. for 1 h. The methanol was removed under reduced pressure and ethyl acetate was added. The organic phase was separated and concentrated. The residue was purified by flash silica chromatography (eluent: 3% methanol in ethyl acetate) followed by preparatory HPLC (Gilson 281, Xbridge 21.2*250 mm c18, 10 um, A: water (10 mL ammonium bicarbonate) B: acetonitrile, 25-75% B over 10 min) to afford N-[6-[4-(hydroxymethyl)-1-piperidyl]-2,2-dimethyl-3H-furo[2,3-b]pyridin-5-yl]-6-methyl-pyrazolo[1,5-a]pyrimidine-3-carboxamide (100 mg, 0.23 mmol, 42.4% yield) as a white solid. $^1$H NMR (400 MHz, CDCl$_3$): 10.12 (s, 1H), 8.69 (s, 1H), 8.63 (s, 2H), 8.61 (s, 1H), 3.64-3.61 (m, 2H), 3.29-3.26 (m, 2H), 3.03 (s, 2H), 2.94-2.88 (m, 2H), 2.48 (s, 3H), 2.01 (s, 2H), 1.81-1.79 (m, 2H), 1.65-1.63 (m, 1H), 1.51 (s, 6H), 1.37-1.34 (m, 1H). MS (ESI): m/z=437.1[M+1]$^+$.

Example 4

N-(6-(4-(2-Hydroxyethyl)piperazin-1-yl)-2,2-dimethyl-2,3-dihydrofuro[2,3-b]pyridin-5-yl)pyrazolo[1,5-a]pyrimidine-3-carboxamide

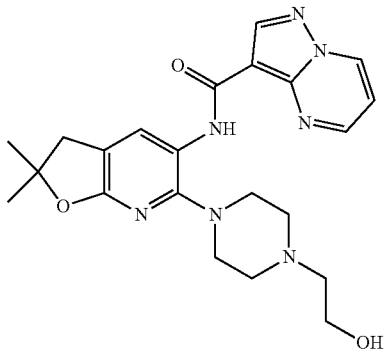 [SMILES: CC1(C)Cc2cc(NC(=O)c3cnn4cccnc34)c(N3CCN(CCO)CC3)nc2O1]

Step A. 2-[4-(2,2-Dimethyl-5-nitro-3H-furo[2,3-b]pyridin-6-yl)piperazin-1-yl]ethanol

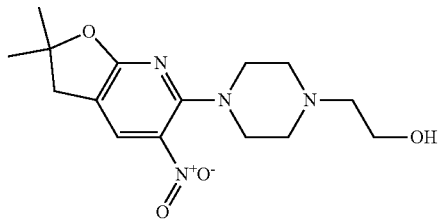

A mixture of cesium carbonate (738.1 mg, 2.26 mmol) 6-fluoro-2,2-dimethyl-5-nitro-3H-furo[2,3-b]pyridine (Example 1, Step C, 350 mg, 1.13 mmol), 1-piperazine ethanol (154.8 mg, 1.2 mmol) in acetonitrile (20 ml) was stirred at rt for 3 h. Water was added and the mixture was extracted with ethyl acetate (40 mL). The organic phase was isolated and concentrated to afford 2-[4-(2,2-dimethyl-5-nitro-3H-furo[2,3-b]pyridin-6-yl)piperazin-1-yl]ethanol (300 mg, 0.81 mmol, 71.4% yield) as a yellow oil. MS (ESI): m/z=323.3[M+H]$^+$.

Step B. 2[4-(5-Amino-2,2-dimethyl-3H-furo[2,3-b]pyridin-6-yl)piperazin-1-yl]ethanol

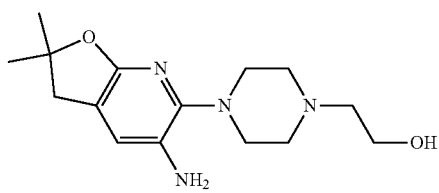

A mixture of palladium on carbon (10 wt %, 100 mg, 0.93 mmol) and 2-[4-(2,2-dimethyl-5-nitro-3H-furo[2,3-b]pyridin-6-yl)piperazin-1-yl]ethanol (300 mg, 0.93 mmol) in methanol (20 mL) was stirred at rt under an atmosphere of hydrogen for 2 h. The reaction was filtered and the filtrate was concentrated to afford 2-[4-(5-amino-2,2-dimethyl-3H-furo[2,3-b]pyridin-6-yl)piperazin-1-yl]ethanol (240 mg, 65.3% yield) as a brown oil. MS (ESI): m/z=293.2 [M+H]$^+$.

Step C. N-(6-(4-(2-Hydroxyethyl)piperazin-1-yl)-2,2-dimethyl-2,3-dihydrofuro[2,3-b]pyridin-5-yl)pyrazolo[1,5-a]pyrimidine-3-carboxamide

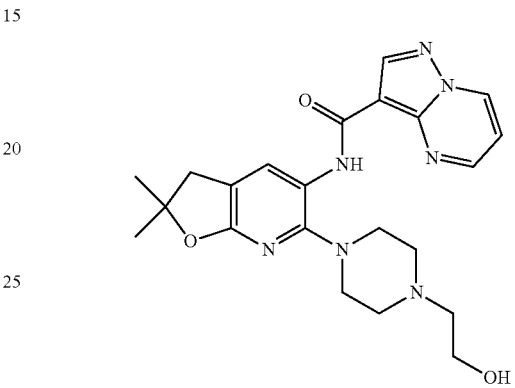

The title compound was made in a manner analogous to Example 1, Step F to give N-(6-(4-(2-hydroxyethyl)piperazin-1-yl)-2,2-dimethyl-2,3-dihydrofuro[2,3-b]pyridin-5-yl)pyrazolo[1,5-a]pyrimidine-3-carboxamide (115 mg, 32% yield) as a light yellow solid. $^1$H NMR (400 MHz, CDCl$_3$): 10.01 (s, 1H), 8.84 (d, J=7.2 Hz, 1H), 8.78 (s, 1H), 8.74 (d, J=4.0 Hz, 1H), 8.57 (s, 1H), 7.08 (dd, J=4.0, 7.2 Hz, 1H), 3.64 (t, J=5.2 Hz, 2H), 3.19-3.16 (m, 4H), 3.04 (s, 2H), 2.74-2.71 (m, 4H), 2.62 (t, J=5.2 Hz, 2H), 2.02-1.99 (m, 1H), 1.52 (s, 6H). MS (ESI): m/z=438.3[M+1]$^+$.

Example 5

N-[6-[4-Fluoro-4-(hydroxymethyl)-1-piperidyl]-2,2-dimethyl-3H-furo[2,3-b]pyridin-5-yl]pyrazolo[1,5-a]pyrimidine-3-carboxamide

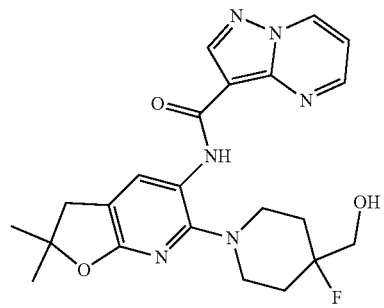 [SMILES: CC1(C)Cc2cc(NC(=O)c3cnn4cccnc34)c(N3CCC(F)(CO)CC3)nc2O1]

Step A. [1-(2,2-Dimethyl-5-nitro-3H-furo[2,3-b]pyridin-6-yl)-4-fluoro-4-piperidyl]methanol

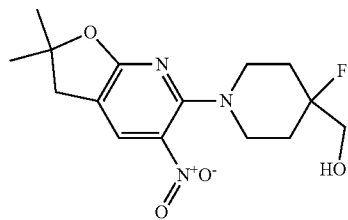

A mixture of potassium carbonate (27.6 mg, 0.2 mmol) 6-fluoro-2,2-dimethyl-5-nitro-3H-furo[2,3-b]pyridine (Example 1, Step C, 21.2 mg, 0.10 mmol), (4-fluoro-4-piperidyl)methanol (13.3 mg, 0.10 mmol) in acetonitrile (1 ml) was stirred at rt for 4 h. The reaction was filtered and the filtrate was concentrated to afford [1-(2,2-dimethyl-5-nitro-3H-furo[2,3-b]pyridin-6-yl)-4-fluoro-4-piperidyl]methanol (40 mg, 91% yield) as a yellow oil. MS (ESI): m/z=326.2 [M+H]⁺.

Step B. [1-(5-Amino-2,2-dimethyl-3H-furo[2,3-b]pyridin-6-yl)-4-fluoro-4-piperidyl]methanol

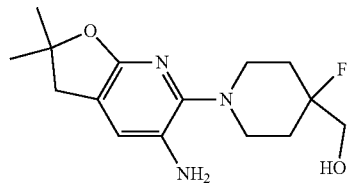 [SMILES: CC1(C)Cc2cc(N)c(N3CCC(F)(CO)CC3)nc2O1]

The title compound was made in a manner analogous to Example 4, Step B to give [1-(5-amino-2,2-dimethyl-3H-furo[2,3-b]pyridin-6-yl)-4-fluoro-4-piperidyl]methanol (55 mg, 77% yield) as a light yellow solid. MS (ESI): m/z=296.1 [M+H]⁺.

Step C. N-[6-[4-Fluoro-4-(hydroxymethyl)-1-piperidyl]-2,2-dimethyl-3H-furo[2,3-b]pyridin-5-yl]pyrazolo[1,5-a]pyrimidine-3-carboxamide

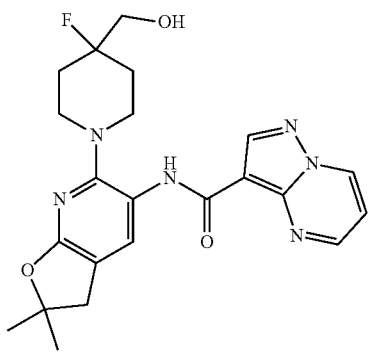 [SMILES: CC1(C)Cc2cc(NC(=O)c3cnn4cccnc34)c(N3CCC(F)(CO)CC3)nc2O1]

A mixture of pyrazolo[1,5-a]pyrimidine-3-carboxylic acid (36.5 mg, 0.22 mmol), [1-(5-amino-2,2-dimethyl-3H-furo[2,3-b]pyridin-6-yl)-4-fluoro-4-piperidyl]methanol (55.0 mg, 0.19 mmol), HATU (106.2 mg, 0.28 mmol), N,N-diisopropylethylamine (37.7 mg, 0.37 mmol) in N,N-dimethylformamide (2 ml) was stirred at 80° C. for 4 h. The reaction was filtered and the filtrate was purified by preparative HPLC to give N-[6-[4fluoro-4-(hydroxymethyl)-1-piperidyl]-2,2-dimethyl-3H-furo[2,3-b]pyridin-5-yl]pyrazolo[1,5-a]pyrimidine-3-carboxamide (56 mg, 68% yield) as a white solid. ¹H NMR (400 MHz, DMSO-$d_6$) δ 10.13 (d, J=1.6 Hz, 1H), 9.39 (dt, J=7.0, 1.3 Hz, 1H), 8.90 (dd, J=4.0, 1.6 Hz, 1H), 8.70 (d, J=1.4 Hz, 1H), 8.59 (d, J=1.3 Hz, 1H), 7.35 (dd, J=7.1, 4.2 Hz, 1H), 5.14 (t, J=5.9 Hz, 1H), 3.52 (dd, J=17.6, 5.9 Hz, 2H), 3.07-2.91 (m, 6H), 2.13-1.92 (m, 2H), 1.83 (t, J=12.1 Hz, 2H), 1.44 (s, 6H). MS (ESI): m/z=441.1 [M+H]⁺.

Example 6

N-[6-[4-(2-amino-2-oxo-ethyl)piperazin-1-yl]-2,2-dimethyl-3H-furo[2,3-b]pyridin-5-yl]pyrazolo[1,5-a]pyrimidine-3-carboxamide

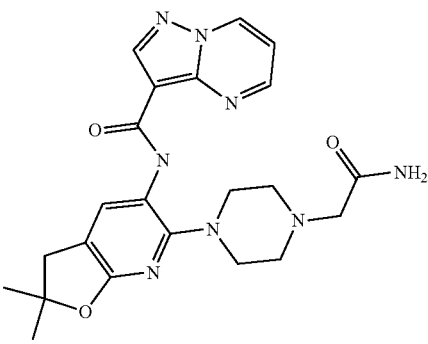 [SMILES: CC1(C)Cc2cc(NC(=O)c3cnn4cccnc34)c(N3CCN(CC(N)=O)CC3)nc2O1]

Step A. tert-Butyl 4-(2,2-dimethyl-5-nitro-3H-furo[2,3-b]pyridin-6-yl)piperazine-1-carboxylate

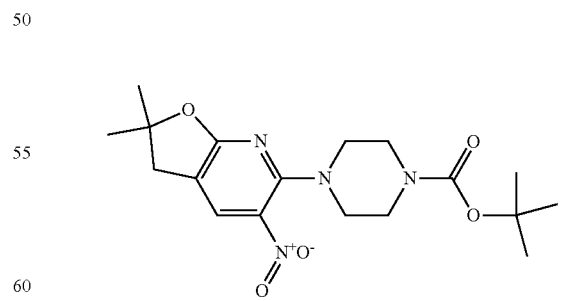

The title compound was made in a manner analogous to Example 5, Step A to give tert-butyl 4-(2,2-dimethyl-5-nitro-3H-furo[2,3-b]pyridin-6-yl)piperazine-1-carboxylate (40 mg, 91% yield) as a yellow solid. MS (ESI): m/z=379.2 [M+H]⁺.

Step B. 2,2-Dimethyl-5-nitro-6-piperazin-1-yl-3H-furo[2,3-b]pyridine hydrochloride

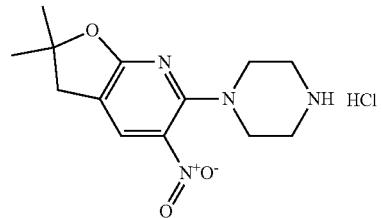

A mixture of hydrochloric acid (0.3 mL, 1.1 mmol) and tert-butyl 4-(2,2-dimethyl-5-nitro-3H-furo[2,3-b]pyridin-6-yl)piperazine-1-carboxylate (85.0 mg, 0.220 mmol) in 1,4-dioxane (1 mL) was stirred at rt for 4 h. The reaction was concentrated to give 2,2-dimethyl-5-nitro-6-piperazin-1-yl-3H-furo[2,3-b]pyridine as the hydrochloride salt as a yellow solid (70 mg, 99% yield). MS (ESI): m/z=279.1 [M+H]$^+$.

Step C. 2-[4-(2,2-Dimethyl-5-nitro-3H-furo[2,3-b]pyridin-6-yl)piperazin-1-yl]acetamide

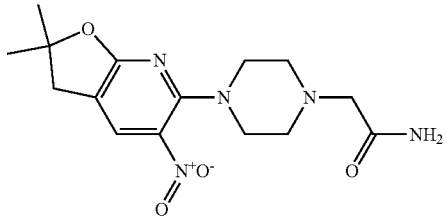

A mixture of 2,2-dimethyl-5-nitro-6-piperazin-1-yl-3H-furo[2,3-b]pyridine hydrochloride (70.0 mg, 0.22 mmol) and 2-chloroacetamide (31.2 mg, 0.33 mmol) in acetonitrile (2 ml) was stirred at rt for 4 h. The reaction was concentrated to give the desired product as a yellow solid. MS (ESI): m/z=336.1 [M+H]$^+$.

Step D. 2-[4-(5-Amino-2,2-dimethyl-3H-furo[2,3-b]pyridin-6-yl)piperazin-1-yl]acetamide

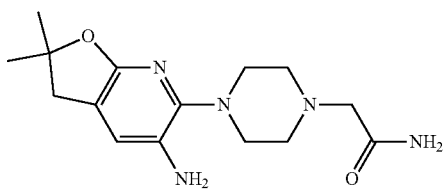

The title compound was made in a manner analogous to Example 4, Step B to give 2-[4-(5-amino-2,2-dimethyl-3H-furo[2,3-b]pyridin-6-yl)piperazin-1-yl]acetamide (66 mg, 95% yield) as a yellow solid. MS (ESI): m/z=306.1 [M+H]$^+$.

Step E. N-[6-[4-(2-Amino-2-oxo-ethyl)piperazin-1-yl]-2,2-dimethyl-3H-furo[2,3-b]pyridin-5-yl]pyrazolo[1,5-a]pyrimidine-3-carboxamide

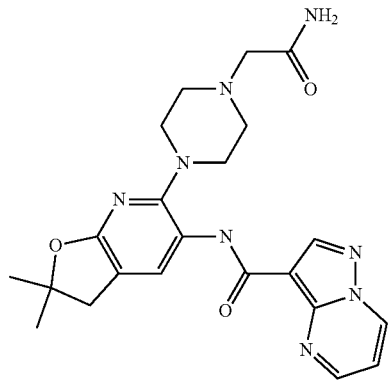 [SMILES: CC1(C)Cc2cc(NC(=O)c3cnn4cccnc34)c(N3CCN(CC(N)=O)CC3)nc2O1]

The title compound was made in a manner analogous to Example 5, Step C to give N-[6-[4-(2-amino-2-oxo-ethyl)piperazin-1-yl]-2,2-dimethyl-3H-furo[2,3-b]pyridin-5-yl]pyrazolo[1,5-a]pyrimidine-3-carboxamide (55 mg, 62% yield) as a yellow solid. $^1$H NMR (400 MHz, DMSO-d$_6$) δ 10.08 (s, 1H), 9.39 (d, J=6.9 Hz, 1H), 8.99 (d, J=4.2 Hz, 1H), 8.70 (s, 1H), 8.57 (s, 1H), 7.37 (dd, J=7.2, 4.2 Hz, 1H), 7.28-7.22 (m, 1H), 7.17 (s, 1H), 3.06-2.95 (m, 8H), 2.69 (t, J=4.8 Hz, 4H), 1.44 (s, 6H). MS (ESI): m/z=441.1 [M+H]$^+$.

Examples 7 and 8

(R)—N-(6-(3-(Hydroxymethyl)morpholino)-2,2-dimethyl-2,3-dihydrofuro[2,3-b]pyridin-5-yl)pyrazolo[1,5-a]pyrimidine-3-carboxamide and (S)—N-(6-(3-(Hydroxymethyl)morpholino)-2,2-dimethyl-2,3-dihydrofuro[2,3-b]pyridin-5-yl)pyrazolo[1,5-a]pyrimidine-3-carboxamide

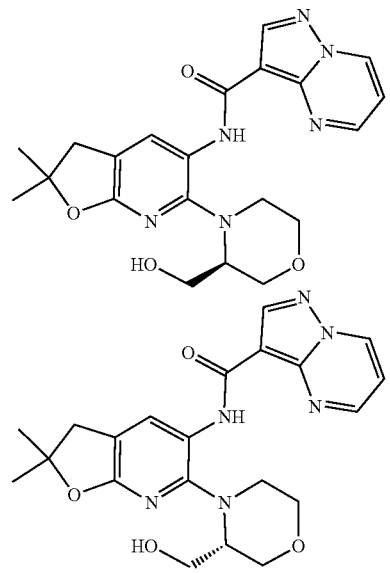

Step A. (4-(2,2-dimethyl-5-nitro-2,3-dihydrofuro[2,3-b]pyridin-6-yl)morpholin-3-yl)methanol

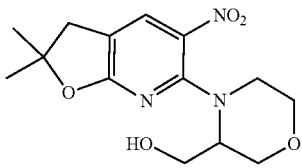 [SMILES: CC1(C)Cc2cc([N+](=O)[O-])c(N3CCOCC3CO)nc2O1]

A mixture of 6-fluoro-2,2-dimethyl-5-nitro-3H-furo[2,3-b]pyridine (Example 1, Step C; 170 mg, 0.80 mmol), morpholin-3-ylmethanol (235 mg, 2.0 mmol) and N,N-diisopropylethylamine (0.13 mL, 0.8 mmol) in acetonitrile (4 mL) was heated on a sealed vial at 60° C. for 1 h. The mixture was filtered, the filtrate concentrated in vacuo and the yellow residue partitioned between 1% aqueous citric acid and ethyl acetate. The organic phase was isolated and washed with water and brine, dried over magnesium sulfate and concentrated. The yellow residue was purified by silica gel chromatography (eluting gradient 0-50% isopropyl acetate: heptanes) to afford (1-(2,2-dimethyl-5-nitro-2,3-dihydrofuro[2,3-b]pyridin-6-yl)piperidin-4-yl)methanol as a yellow foam MS (ESI): m/z=310 [M+1]$^+$.

Step B. (4-(5-amino-2,2-dimethyl-2,3-dihydrofuro[2,3-b]pyridin-6-yl)morpholin-3-yl)methanol

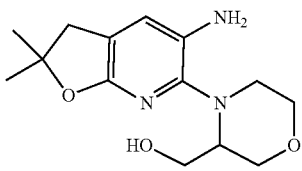 [SMILES: CC1(C)Cc2cc(N)c(N3CCOCC3CO)nc2O1]

A solution of (4-(2,2-dimethyl-5-nitro-2,3-dihydrofuro[2,3-b]pyridin-6-yl)morpholin-3-yl)methanol (168 mg, 0.54 mmol) in dioxane (12 mL) was treated with 10% palladium on carbon (100 mg) and stirred under an atmosphere of hydrogen for 8 h. The mixture was filtered through celite and the filtrate concentrated to afford (4-(5-amino-2,2-dimethyl-2,3-dihydrofuro[2,3-b]pyridin-6-yl)morpholin-3-yl)methanol (110 mg, 72%) as a colorless foam which was used without further purification. MS (ESI): m/z=280 [M+1]$^+$.

Step C. (R)—N-(6-(3-(Hydroxymethyl)morpholino)-2,2-dimethyl-2,3-dihydrofuro[2,3-b]pyridin-5-yl)pyrazolo[1,5-a]pyrimidine-3-carboxamide and (S)—N-(6-(3-(Hydroxymethyl)morpholino)-2,2-dimethyl-2,3-dihydrofuro[2,3-b]pyridin-5-yl)pyrazolo[1,5-a]pyrimidine-3-carboxamide

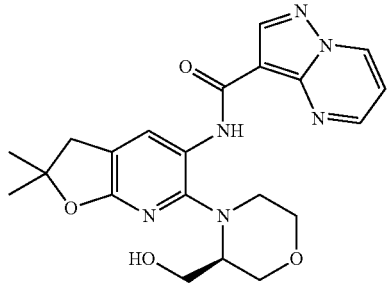

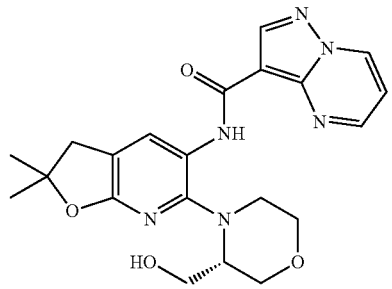

A mixture of (4-(5-amino-2,2-dimethyl-2,3-dihydrofuro[2,3-b]pyridin-6-yl)morpholin-3-yl)methanol (110 mg, 0.39 mmol), pyrazolo[1,5-a]pyrimidine-3-carbonyl chloride hydrochloride (94 mg, 0.43 mmol), 4-dimethylaminopyridine (5 mg, 0.04 mmol) and N,N-diisopropylethylamine (0.135 ml, 0.78 mmol) in pyridine (4 ml) was subjected to microwave heating at 110° C. for 30 min. The mixture was concentrated and the residue partitioned between ethyl acetate and water. The organic phase was isolated, washed with 5% aqueous citric acid, saturated aqueous sodium bicarbonate, water and brine, dried over magnesium sulfate and concentrated. The residue was purified by silica gel chromatography (eluting gradient 0-70% isopropyl acetate: heptanes) to afford N-(2,2-dimethyl-6-morpholino-2,3-dihydrofuro[2,3-b]pyridin-5-yl)pyrazolo[1,5-a]pyrimidine-3-carboxamide (100 mg, 60%) as a mixture of enantiomers. MS (ESI): m/z=425 [M+1]$^+$. The enantiomers were resolved by chiral SFC to give (R)—N-(6-(3-(hydroxymethyl)morpholino)-2,2-dimethyl-2,3-dihydrofuro[2,3-b]pyridin-5-yl)pyrazolo[1,5-a]pyrimidine-3-carboxamide (25 mg) and (S)—N-(6-(3-(hydroxymethyl)morpholino)-2,2-dimethyl-2,3-dihydrofuro[2,3-b]pyridin-5-yl)pyrazolo[1,5-a]pyrimidine-3-carboxamide (27 mg). Stereochemistry was arbitrarily assigned based on peak elution.

Example 7

Peak 1: $^1$H NMR (400 MHz, DMSO-d$_6$) δ 10.42 (s, 1H), 9.38 (dd, J=7.0, 1.6 Hz, 1H), 8.96 (dd, J=4.2, 1.7 Hz, 1H), 8.69 (s, 1H), 8.67-8.62 (m, 1H), 7.35 (dd, J=7.0, 4.2 Hz, 1H), 4.50 (t, J=5.2 Hz, 1H), 4.06 (dd, J=11.2, 2.5 Hz, 1H), 3.80 (dd, J=6.1, 4.1 Hz, 2H), 3.64 (dd, J=11.2, 6.9 Hz, 1H), 3.29-3.21 (m, 3H), 3.07 (s, 2H), 2.95-2.84 (m, 2H), 1.45 (s, 3H), 1.44 (s, 3H). MS (ESI): m/z=425 [M+1]$^+$.

Example 8

Peak 2: 1H NMR (400 MHz, DMSO-d$_6$) δ 10.42 (s, 1H), 9.38 (dd, J=7.0, 1.6 Hz, 1H), 8.96 (dd, J=4.2, 1.6 Hz, 1H), 8.69 (s, 1H), 8.65 (d, J=1.1 Hz, 1H), 7.35 (dd, J=7.0, 4.2 Hz, 1H), 4.50 (t, J=5.2 Hz, 1H), 4.06 (dd, J=11.1, 2.4 Hz, 1H), 3.84-3.77 (m, 2H), 3.64 (dd, J=11.2, 6.9 Hz, 1H), 3.29-3.20 (m, 3H), 3.07 (s, 2H), 2.94-2.83 (m, 2H), 1.46 (s, 3H), 1.44 (s, 3H). MS (ESI): m/z=425 [M+1]$^+$.

Example 9

N-(6-(4-(2,2-Difluoroethyl)piperazin-1-yl)-2,2-dimethyl-2,3-dihydrofuro[2,3-b]pyridin-5-yl)pyrazolo[1,5-a]pyrimidine-3-carboxamide

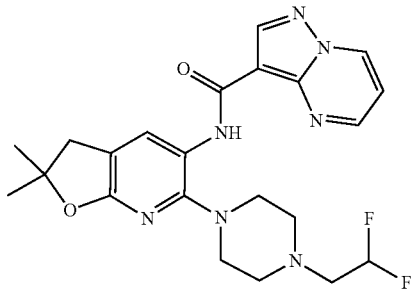 [SMILES: CC1(C)Cc2cc(NC(=O)c3cnn4cccnc34)c(N3CCN(CC(F)F)CC3)nc2O1]

Step A. 6-(4-(2,2-Difluoroethyl)piperazin-1-yl)-2,2-dimethyl-5-nitro-2,3-dihydrofuro[2,3-b]pyridine

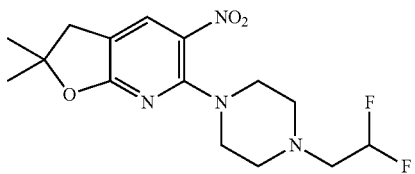

A mixture of 6-fluoro-2,2-dimethyl-5-nitro-3H-furo[2,3-b]pyridine (Example 1, Step C; 170 mg, 0.80 mmol), 1-(2,2-difluoroethyl)piperazine (301 mg, 2.00 mmol) and N,N-diisopropylethylamine (0.132 mL, 0.8 mmol) in acetonitrile (2 mL) was heated in a sealed vial at 60° C. for 20 h. The mixture was filtered, the filtrate concentrated in vacuo and the yellow residue partitioned between water and ethyl acetate. The organic phase was isolated and washed with water and brine, dried over magnesium sulfate and concentrated to afford 6-(4-(2,2-difluoroethyl)piperazin-1-yl)-2,2-dimethyl-5-nitro-2,3-dihydrofuro[2,3-b]pyridine (270 mg, 98.5%) as yellow residue which crystallized upon standing and was used without further purification. MS (ESI): m/z=343 [M+1]$^+$.

Step B. 6-(4-(2,2-Difluoroethyl)piperazin-1-yl)-2,2-dimethyl-2,3-dihydrofuro[2,3-b]pyridin-5-amine

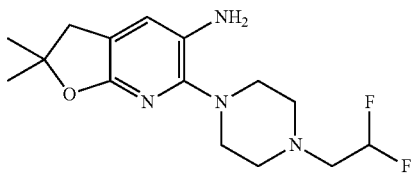 [SMILES: CC1(C)Cc2cc([N+](=O)[O-])c(N3CCN(CC(F)F)CC3)nc2O1]

A solution of 6-(4-(2,2-difluoroethyl)piperazin-1-yl)-2,2-dimethyl-5-nitro-2,3-dihydrofuro[2,3-b]pyridine (270 mg, 0.79 mmol) in dioxane (12 ml) was treated with 10% palladium on carbon (200 mg) and stirred under an atmosphere of hydrogen for 18 h. The mixture was filtered through celite and the filtrate concentrated to 6-(4-(2,2-difluoroethyl)piperazin-1-yl)-2,2-dimethyl-2,3-dihydrofuro[2,3-b]pyridin-5-amine (225 mg, 91%) which was used without further purification. MS (ESI): m/z=313 [M+1]$^+$.

Step C. N-(6-(4-(2,2-Difluoroethyl)piperazin-1-yl)-2,2-dimethyl-2,3-dihydrofuro[2,3-b]pyridin-5-yl)pyrazolo[1,5-a]pyrimidine-3-carboxamide

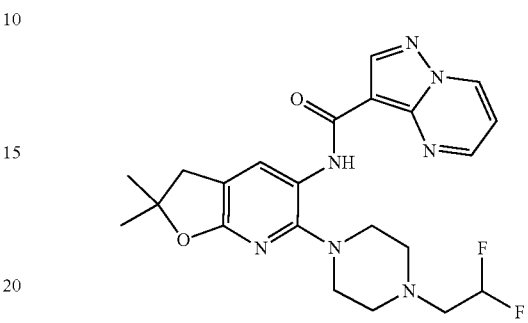

A mixture of 6-(4-(2,2-difluoroethyl)piperazin-1-yl)-2,2-dimethyl-2,3-dihydrofuro[2,3-b]pyridin-5-amine (225 mg, 0.72 mmol), pyrazolo[1,5-a]pyrimidine-3-carbonyl chloride hydrochloride (220 mg, 1.00 mmol), 4-dimethylaminopyridine (18 mg, 0.14 mmol) and N,N-diisopropylethylamine (0.38 ml, 2.20 mmol) in pyridine (5 ml) was subjected to microwave heating at 110° C. for 30 min. The mixture was concentrated and the residue partitioned between ethyl acetate and water. The organic phase was isolated, washed with 1% aqueous citric acid, saturated aqueous sodium bicarbonate, water and brine, dried over magnesium sulfate and concentrated. The residue was purified by silica gel chromatography (eluting gradient 0-100% isopropyl acetate:heptanes) to N-(6-(4-(2,2-difluoroethyl)piperazin-1-yl)-2,2-dimethyl-2,3-dihydrofuro[2,3-b]pyridin-5-yl)pyrazolo[1,5-a]pyrimidine-3-carboxamide (106 mg, 32%). $^1$H NMR (400 MHz, DMSO-d6) δ 10.04 (s, 1H), 9.38 (dd, J=7.0, 1.6 Hz, 1H), 8.96 (dd, J=4.1, 1.6 Hz, 1H), 8.70 (s, 1H), 8.54 (s, 1H), 7.37 (dd, J=7.0, 4.2 Hz, 1H), 6.39-6.02 (m, 1H), 3.00-2.92 (m, 4H), 2.91-2.79 (m, 2H), 2.79-2.73 (m, 4H), 1.44 (s, 6H). MS (ESI): m/z=458 [M+1]$^+$.

Examples 10 and 11

(S)—N-(2-(Hydroxymethyl)-2-methyl-6-morpholino-2,3-dihydrofuro[2,3-b]pyridin-5-yl)pyrazolo[1,5-a]pyrimidine-3-carboxamide and (R)—N-(2-(hydroxymethyl)-2-methyl-6-morpholino-2,3-dihydrofuro[2,3-b]pyridin-5-yl)pyrazolo[1,5-a]pyrimidine-3-carboxamide

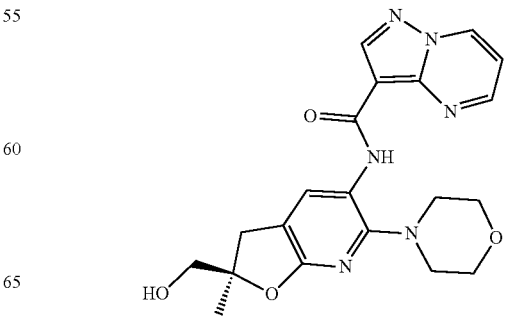

-continued

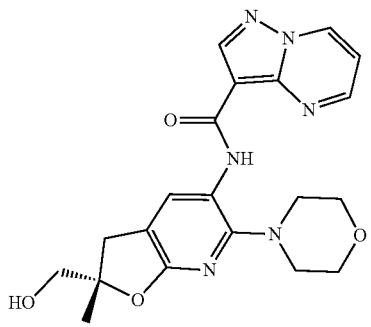

Step A. (2,6-Difluoro-3-pyridyl)methanol

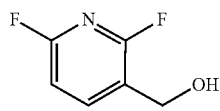

To a solution of 2,6-difluoropyridine-3-carboxylic acid (8 g, 50 mmol) in tetrahydrofuran (100 ml) at 0° C. under nitrogen atmosphere was slowly added 10 M borane in dimethylsulfide (20 ml, 201 mmol). After addition, the reaction mixture was stirred at 10° C. for 3 h, cooled to 0° C., and treated with drop-wise addition of methanol (15 ml). The mixture was heated to 40° C. for 30 min, concentrated and purified by silica gel column (eluting gradient: 8%-10% methanol:dichloromethane) to afford (2,6-difluoro-3-pyridyl)methanol (7.0 g, 96%) as a colorless oil. $^1$H NMR (400 MHz, DMSO-d$_6$) δ 8.18-8.11 (m, 1H), 7.16 (dd, J=8.0 Hz, 2.0 Hz, 1H), 5.47 (t, J=5.2 Hz, 1H), 4.52 (d, J=5.2 Hz, 2H).

Step B. 3-(Bromomethyl)-2,6-difluoro-pyridine

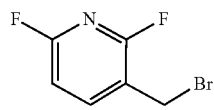

To (2,6-difluoro-3-pyridyl)methanol (7.0 g, 48.2 mmol) in tetrahydrofuran (20 ml) was added triphenylphosphine (15.2 g, 57.9 mmol) at 10° C. After 10 min, tetrabromomethane (19.2 g, 57.9 mmol) was added and the mixture was stirred for 16 h under nitrogen atmosphere at 10° C. The mixture was filtered and the filtrate was purified by flash column chromatography (eluent: 30% ethyl acetate:petroleum ether) to afford 3-(bromomethyl)-2,6-difluoro-pyridine (9.0 g, 90%) as a white solid. $^1$H NMR (400 MHz, CDCl$_3$) δ 7.98-7.90 (m, 1H), 6.85 (dd, J=8.4 Hz, 2.8 Hz, 1H), 4.46 (s, 2H).

Step C. Methyl 2-benzyloxypropanoate

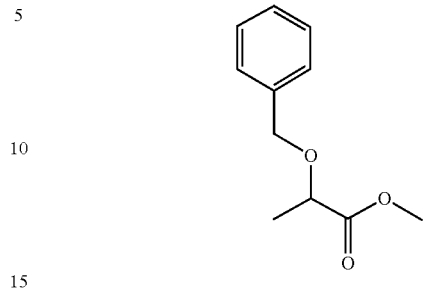

To a solution of methyl lactate (10.0 g, 96.1 mmol) in tetrahydrofuran (100 ml) was added sodium hydride (3.8 g, 96.1 mmol) at 0° C. After 1 h, tetrabutyl ammonium iodide (17.7 mg, 0.05 mmol) and benzyl bromide (11.4 ml, 96.1 mmol) were added and the mixture was allowed to stir at 10° C. for 16 h. The reaction was quenched with chilled saturated ammonium chloride solution (50 ml) and extracted with ethyl acetate (30 ml×2). The combined organic phases were washed with brine (20 ml×2), dried over sodium sulfate and concentrated to dryness. The residue was purified by silica gel column (eluting gradient: 5%-10% ethyl acetate:petroleum ether) to afford methyl 2-benzyloxypropanoate (12 g, 64.3% yield) as colorless oil. $^1$H NMR (300 MHz, CDCl$_3$): δ 7.37-7.32 (m, 5H), 4.72 (d, J=11.6 Hz, 1H), 4.48 (d, J=12.0 Hz, 1H), 4.11 (q, J=6.4 Hz, 1H), 3.77 (s, 3H), 1.46 (d, J=6.8 Hz, 3H).

Step D. Methyl 2-benzyloxy-3-(2,6-difluoro-3-pyridyl)-2-methyl-propanoate

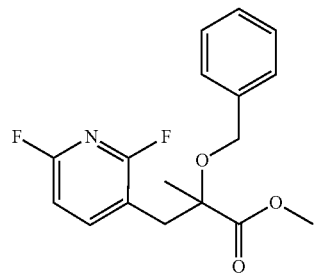 [SMILES: COC(=O)C(C)(Cc1ccc(F)nc1F)OCc1ccccc1]

To a solution of methyl 2-benzyloxypropanoate (11.1 g, 57.1 mmol) in tetrahydrofuran (50 ml) under nitrogen atmosphere and cooled to −70° C. was added lithium diisopropylamide (28.6 ml, 57.1 mmol) drop-wise over 20 min. The mixture was stirred at −70° C. for 1 h and 3-(bromomethyl)-2,6-difluoro-pyridine (10.8 g, 51.9 mmol) in tetrahydrofuran (10 ml) was added slowly at −70° C. After addition, the mixture was warmed to 10° C. and stirred for 16 h. The mixture was quenched with saturated ammonium chloride solution (50 ml), stirred for 20 min and concentrated under reduced pressure. The remaining mixture was extracted with ethyl acetate (50 ml), and the isolated organic phase was washed with brine (20 ml×2), concentrated under reduced pressure and purified by silica gel column chromatography (eluent 20% ethyl acetate:petroleum ether) to afford methyl 2-benzyloxy-3-(2,6-difluoro-3-pyridyl)-2-methyl-propanoate (14.0 g, 84%) as an orange oil. $^1$H NMR (400 MHz, CDCl$_3$) δ 7.85-7.82 (m, 1H), 7.37-7.29 (m, 5H), 6.76-6.74 (m, 1H), 4.51-4.46 (m, 2H), 3.76 (s, 3H), 3.14-3.11 (m, 2H), 1.53 (s, 3H).

Step E. Methyl 3-(2,6-difluoro-3-pyridyl)-2-hydroxy-2-methyl-propanoate

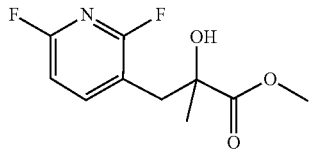 [SMILES: COC(=O)C(C)(O)Cc1ccc(F)nc1F]

Methyl 2-benzyloxy-3-(2,6-difluoro-3-pyridyl)-2-methyl-propanoate (13.0 g, 40.5 mmol) in methanol (50 ml) was treated with 10% palladium on carbon (5.0 g, 4.7 mmol) and placed under a hydrogen atmosphere at 40 psi at 65° C. for 5 h. The mixture was cooled to room temperature, filtered through celite, concentrated and purified by silica gel column (eluting gradient: 20%-30% ethyl acetate: petroleum ether) to afford methyl 3-(2,6-difluoro-3-pyridyl)-2-hydroxy-2-methyl-propanoate (8.3 g, 89%) as a white crystalline solid. $^1$H NMR (400 MHz, CDCl$_3$) δ 7.89-7.82 (m, 1H), 6.79 (dd, J=8.0 Hz, 2.8 Hz, 1H), 3.80 (s, 3H), 3.21 (s, 1H), 3.13 (d, J=14.0 Hz, 1H), 2.95 (d, J=14.0 Hz, 1H), 1.49 (s, 3H).

Step F. Methyl 6-fluoro-2-methyl-3H-furo[2,3-b]pyridine-2-carboxylate

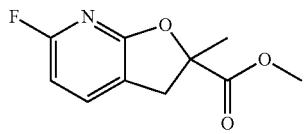

To methyl 3-(2,6-difluoro-3-pyridyl)-2-hydroxy-2-methyl-propanoate (7.3 g, 31.6 mmol) in tetrahydrofuran (50 L) was added 4 Å molecular sieves (200 mg) followed by sodium hydride (60% in mineral oil, 2.8 g, 69.5 mmol) in portions at 10° C. The mixture was stirred for 20 h, cooled to 0° C. and poured over a chilled saturated ammonium chloride solution (50 ml). The resulting mixture was extracted with ethyl acetate (50 ml) and the isolated organic phase was washed with brine (40 ml×2), dried over sodium sulfate, concentrated to dryness and purified by silica gel column (eluting gradient: 20%-30% ethyl acetate: petroleum ether) to afford methyl 6-fluoro-2-methyl-3H-furo[2,3-b]pyridine-2-carboxylate (6.2 g, 93%) as a light yellow oil. $^1$H NMR (400 MHz, CDCl$_3$) δ 7.53-7.49 (m, 1H), 6.46 (dd, J=7.6 Hz, 1.6 Hz, 1H), 3.79 (s, 3H), 3.62 (d, J=16.4 Hz, 1H), 3.15 (d, J=16.4 Hz, 1H), 1.75 (s, 3H). LCMS (ESI): m/z=211.9 [M+H]$^+$.

Step G. (6-Fluoro-2-methyl-2,3-dihydrofuro[2,3-b]pyridin-2-yl)methanol

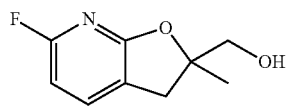

To a solution of ethyl 6-fluoro-2-methyl-3H-furo[2,3-b]pyridine-2-carboxylate (1.0 g, 4.44 mmol) in tetrahydrofuran (10 ml) and ethanol (5 ml) was added lithium borohydride (242 mg, 11.1 mmol). The mixture was stirred at 20° C. for 3 h. The reaction was quenched with water (5 ml) and concentrated under reduced pressure to remove the tetrahydrofuran. The remaining mixture was extracted with ethyl acetate (50 ml×3) and the combined organic phases were washed with brine (20 ml), dried over sodium sulfate filtered and concentrated to give (6-fluoro-2-methyl-2,3-dihydrofuro[2,3-b]pyridin-2-yl) methanol (800 mg, 98%) as white solid. LCMS (ESI): m/z=183.7 [M+H]$^+$.

Step H. (2-Methyl-6-morpholino-2,3-dihydrofuro[2,3-b]pyridin-2-yl)methanol

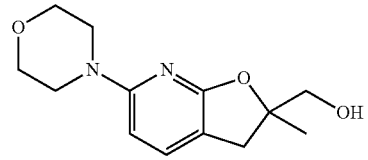 [SMILES: CC1(CO)Cc2ccc(N3CCOCC3)nc2O1]

A mixture of (6-fluoro-2-methyl-2,3-dihydrofuro[2,3-b]pyridin-2-yl)methanol (700 mg, 3.82 mmol) and morpholine (6 ml, 68.87 mmol) was stirred at 100° C. for 35 h, concentrated under reduced pressure and purified by silica gel column chromatography (eluent: 45% ethyl acetate: petroleum ether) to give (2-methyl-6-morpholino-2,3-dihydrofuro[2,3-b]pyridin-2-yl)methanol (0.63 g, 66%) as a white solid. LCMS (ESI): m/z=250.8 [M+H]$^+$.

Step I. (2-Methyl-6-morpholino-5-nitro-2,3-dihydrofuro[2,3-b]pyridin-2-yl)methyl nitrate

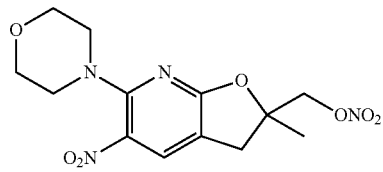

To a solution of (2-methyl-6-morpholino-2,3-dihydrofuro[2,3-b]pyridin-2-yl)methanol (1.5 ml) and acetic anhydride (3 ml) was added copper(II) nitrate (1.05 g, 5.61 mmol) at 0° C. The mixture was stirred at 20° C. for 20 min, diluted with ethyl acetate, poured into ice water and the pH was adjusted to 8 with saturated solution of sodium bicarbonate. The mixture was extracted with ethyl acetate (30 ml×3) and the combined organic phases were dried over sodium sulfate, concentrated under reduced pressure, and purified by silica gel column chromatography (eluent: 35% ethyl acetate: petroleum ether) to give (2-methyl-6-morpholino-5-nitro-2,3-dihydrofuro[2,3-b]pyridin-2-yl)methyl nitrate (190 mg, 30%) as a yellow solid. LCMS (ESI): m/z=340.8 [M+H]$^+$.

Step J. (5-Amino-2-methyl-6-morpholino-2,3-dihydrofuro[2,3-b]pyridin-2-yl)methanol

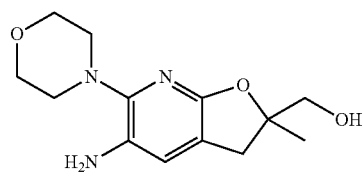 [SMILES: CC1(CO)Cc2cc(N)c(N3CCOCC3)nc2O1]

To a solution of (2-methyl-6-morpholino-5-nitro-2,3-dihydrofuro[2,3-b]pyridin-2-yl)methyl nitrate (0.19 g, 0.56 mmol) in ethanol (10 ml) was added 10% palladium on carbon (40 mg) and the mixture was stirred at 20° C. under an atmosphere of hydrogen (15 psi) over 15 h. The reaction mixture was filtered through celite and concentrated under reduced pressure to give (5-amino-2-methyl-6-morpholino-2,3-dihydro furo[2,3-b]pyridin-2-yl)methanol (0.15 g) as a light yellow solid.

Step K. N-(2-(Hydroxymethyl)-2-methyl-6-morpholino-2,3-dihydrofuro[2,3-b]pyridin-5-yl) pyrazolo[1,5-a]pyrimidine-3-carboxamide

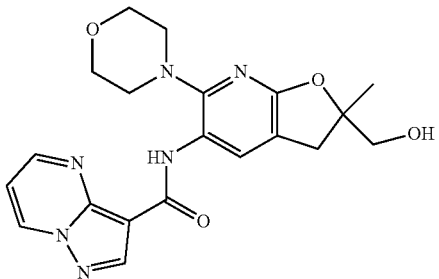 [SMILES: CC1(CO)Cc2cc(NC(=O)c3cnn4cccnc34)c(N3CCOCC3)nc2O1]

A mixture of (5-amino-2-methyl-6-morpholino-2,3-dihydro furo[2,3-b]pyridin-2-yl)methanol (0.15 g, 0.55 mmol), pyrazolo[1,5-a]pyrimidine-3-carbonyl chloride (129 mg, 0.71 mmol), 4-dimethyl aminopyridine (13 mg, 0.11 mmol) and N,N-diisopropylethylamine (141 mg, 1.09 mmol) in N,N-dimethylformamide (5 ml) was irradiated under microwave conditions at 110° C. for 30 min. After being cooled to room temperature, the reaction mixture was concentrated and purified by preparatory TLC (eluent: 9% methanol:dichloromethane) to give N-(2-(hydroxymethyl)-2-methyl-6-morpholino-2,3-dihydrofuro[2,3-b]pyridin-5-yl) pyrazolo[1,5-a]pyrimidine-3-carboxamide (110 mg, 49%) as a yellow solid. LCMS (ESI): m/z=410.9 [M+H]$^+$.

Step L. (S)—N-(2-(Hydroxymethyl)-2-methyl-6-morpholino-2,3-dihydrofuro[2,3-b]pyridin-5-yl)pyrazolo[1,5-a]pyrimidine-3-carboxamide and (R)—N-(2-(hydroxymethyl)-2-methyl-6-morpholino-2,3-dihydrofuro[2,3-b]pyridin-5-yl)pyrazolo[1,5-a]pyrimidine-3-carboxamide

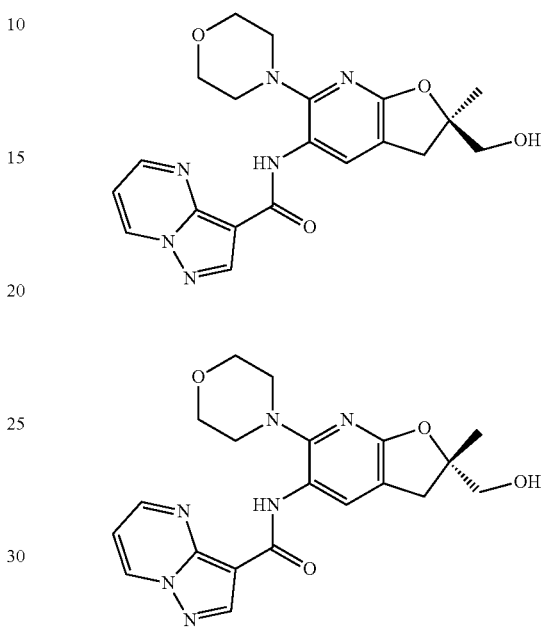

N-(2-(Hydroxymethyl)-2-methyl-6-morpholino-2,3-dihydrofuro[2,3-b]pyridin-5-yl) pyrazolo[1,5-a]pyrimidine-3-carboxamide (140 mg, 0.34 mmol) was resolved by chiral SFC (AD, 250 mm*30 mm, 10 um, supercritical CO$_2$/50% ammonium hydroxide in methanol, 80 ml/min) to afford (S)—N-(2-(Hydroxymethyl)-2-methyl-6-morpholino-2,3-dihydrofuro[2,3-b]pyridin-5-yl)pyrazolo[1,5-a]pyrimidine-3-carboxamide (52 mg, 36%, RT=5.61 min) and (R)—N-(2-(hydroxymethyl)-2-methyl-6-morpholino-2,3-dihydrofuro[2,3-b]pyridin-5-yl)pyrazolo[1,5-a]pyrimidine-3-carboxamide (52 mg, 37%, RT=7.17 min) as yellow solids. Stereochemistry was arbitrarily assigned based on peak elution.

Example 10 peak 1, $^1$H NMR (400 MHz, CD$_3$OD): δ 9.14 (dd, J=7.2, 1.6 Hz, 1H), 8.92 (dd, J=4.0, 1.6 Hz, 1H), 8.65 (s, 1H), 8.51 (s, 1H), 7.30 (dd, J=7.2, 4.0 Hz, 1H), 3.90 (t, J=4.8 Hz, 4H), 3.65-3.60 (m, 2H), 3.34 (dd, J=16.4, 1.2 Hz, 1H), 3.04 (t, J=4.8 Hz, 4H), 2.97 (dd, J=16.4, 1.2 Hz, 1H), 1.46 (s, 3H).

Example 11 peak 2, $^1$H NMR (400 MHz, CD$_3$OD): δ 9.14-9.12 (dd, J=6.8, 1.6 Hz, 1H), 8.92 (dd, J=4.0, 1.6 Hz, 1H), 8.65 (s, 1H), 8.51 (s, 1H), 7.30-7.27 (dd, J=6.8, 4.0 Hz, 1H), 3.90 (t, J=4.8 Hz, 4H), 3.68 (d, J=12.0 Hz, 1H), 3.60 (d, J=12.0 Hz, 1H), 3.34 (dd, J=16.4, 1.2 Hz, 1H), 3.04 (t, J=4.8 Hz, 4H), 2.97 (dd, J=16.4, 1.2 Hz, 1H), 1.46 (s, 3H).

Example 12

N-(6-Methyl-2-morpholino-7-oxo-6,7-dihydro-5H-pyrrolo[3,4-b]pyridin-3-yl)pyrazolo[1,5-a]pyrimidine-3-carboxamide

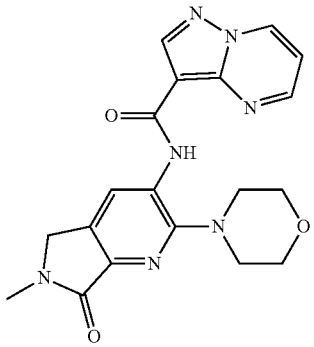 [SMILES: CN1Cc2cc(NC(=O)c3cnn4cccnc34)c(N3CCOCC3)nc2C1=O]

Step A. Methyl 3-(Bromomethyl)-6-chloro-pyridine-2-carboxylate

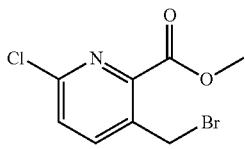

To a solution of methyl 6-chloro-3-methyl-pyridine-2-carboxylate (5.0 g, 26.94 mmol) and 1-bromo-2,5-pyrrolidinedione (4.8 g, 26.94 mmol) in carbon tetrachloride (10 ml) under nitrogen atmosphere was added azobisisobutyronitrile (0.44 g, 2.69 mmol). The mixture was stirred at 80° C. for 16 h, diluted with water (50 ml) and extracted with ethyl acetate (100 ml×3). The combined organic phases were washed with brine (100 ml×2), dried over sodium sulfate, filtered and concentrated. The residue was purified by silica gel column chromatography (eluent: 20% ethyl acetate: petroleum ether) to afford methyl 3-(bromomethyl)-6-chloro-pyridine-2-carboxylate (5.3 g, 37%) as a white solid. $^1$H NMR (400 MHz, CDCl$_3$): δ 7.86 (d, J=8.0 Hz, 1H), 7.50 (d, J=8.0 Hz, 1H), 4.89 (s, 2H), 4.03 (s, 3H).

Step B. 2-Chloro-6-methyl-5H-pyrrolo[3,4-b]pyridin-7-one

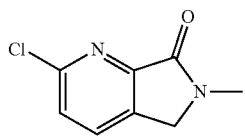

To a solution of methyl 3-(bromomethyl)-6-chloro-pyridine-2-carboxylate (3.0 g, 5.67 mmol) and triethylamine (1.15 g, 11.34 mmol) in methanol (50 ml) was added methylamine (11.3 ml, 22.68 mmol, 2N in methanol). The reaction was stirred at 70° C. for 16 h, concentrated and purified by silica gel column chromatography (eluent: 100% ethyl acetate) to afford 2-chloro-6-methyl-5H-pyrrolo[3,4-b]pyridin-7-one (0.9 g, 87%) as a white solid.

Step C. 6-Methyl-2-morpholino-5H-pyrrolo[3,4-b]pyridin-7-one

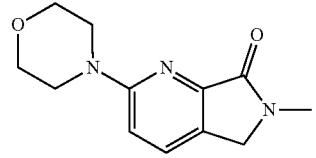 [SMILES: CN1Cc2ccc(N3CCOCC3)nc2C1=O]

A mixture of 2-chloro-6-methyl-5H-pyrrolo[3,4-b]pyridin-7-one (0.9, 4.93 mmol) in morpholine (10 ml) was stirred at 90° C. for 16 h, diluted with water (20 ml) and extracted with ethyl acetate (100 ml×2). The organic phases were isolated, washed with brine (100 ml×2), dried over sodium sulfate, filtered, concentrated and purified by silica gel column chromatography (eluent: 100% ethyl acetate) to afford 6-methyl-2-morpholino-5H-pyrrolo[3,4-b]pyridin-7-one (400 mg, 35%) as a white solid. $^1$H NMR (400 MHz, CDCl$_3$): δ 7.58 (d, J=8.8 Hz, 1H), 6.76 (d, J=8.0 Hz, 1H), 4.26 (s, 2H), 3.83 (t, J=4.8 Hz, 4H), 3.64 (t, J=4.8 Hz, 4H), 3.24 (s, 3H).

Step D. 6-Methyl-2-morpholino-3-nitro-5H-pyrrolo[3,4-b]pyridin-7-one

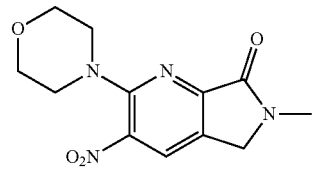 [SMILES: CN1Cc2cc([N+](=O)[O-])c(N3CCOCC3)nc2C1=O]

To a solution of 6-methyl-2-morpholino-5H-pyrrolo[3,4-b]pyridin-7-one (400 mg, 1.71 mmol) in acetic anhydride (10 ml) and acetic acid (5 ml) was added copper (II) nitrate (0.97 g, 5.14 mmol) at 0° C. The reaction was stirred at 25° C. for 2 h. The reaction was diluted with water (20 ml) and extracted with ethyl acetate (100 ml×3). The combined organic phases were washed with brine (100 ml×2), dried over sodium sulfate, filtered, concentrated to dryness and purified by preparatory TLC (eluent: 100% ethyl acetate) to afford 6-methyl-2-morpholino-3-nitro-5H-pyrrolo[3,4-b]pyridin-7-one (350 mg, 74%) as a yellow solid. $^1$H NMR (400 MHz, CDCl$_3$): δ 8.21 (s, 1H), 4.36 (s, 2H), 3.82 (t, J=4.8 Hz, 4H), 3.57 (t, J=4.8 Hz, 4H), 3.27 (s, 3H).

Step E. 5-Amino-2-(2-hydroxy-1,1-dimethyl-ethyl)-6-morpholino-isoindolin-1-one

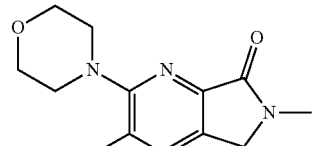

To a solution of 6-methyl-2-morpholino-3-nitro-5H-pyrrolo[3,4-b]pyridin-7-one (0.35 g, 1.26 mmol) and iron dust (351 mg, 6.29 mmol) in ethanol (10 ml) and water (10 ml) was added ammonium chloride (336 mg, 6.29 mmol). The reaction was stirred at 80° C. for 30 min, filtered and concentrated to remove the ethanol. The remaining mixture was washed with dichloromethane (20 ml) and the organic phase was isolated and concentrated to afford 3-amino-6-methyl-2-morpholino-5H-pyrrolo[3,4-b] pyridin-7-one (300 mg, 96%) as a brown solid.

Step F. N-(6-Methyl-2-morpholino-7-oxo-5H-pyrrolo[3,4-b]pyridin-3-yl)pyrazolo[1,5-a]pyrimidine-3-carboxamid

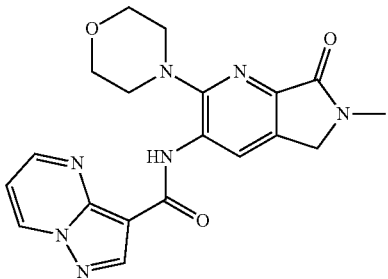 [SMILES: CN1Cc2cc(NC(=O)c3cnn4cccnc34)c(N3CCOCC3)nc2C1=O]

To a solution of 3-amino-6-methyl-2-morpholino-5H-pyrrolo[3,4-b]pyridin-7-one (150 mg, 0.60 mmol) in pyridine (50 ml) was added pyrazolo[1,5-a]pyrimidine-3-carbonyl chloride (165 mg, 0.91 mmol). The reaction was stirred at 25° C. for 6 h, concentrated and purified by reverse phase chromatography (Diamonsil, 150*20 mm*5 um, acetonitrile 10-40%/0.1% formic acid in water) to afford N-(6-methyl-2-morpholino-7-oxo-5H-pyrrolo[3,4-b]pyridin-3-yl)pyrazolo[1,5-a]pyrimidine-3-carboxamide (23.1 mg, 10%) as a brown solid. $^1$H NMR (400 MHz, CDCl$_3$): 10.57 (s, 1H), 9.08 (s, 1H), 8.90-8.88 (m, 1H), 8.86-8.85 (m, 1H), 8.81 (s, 1H), 7.17-7.14 (m, 1H), 4.37 (s, 2H), 4.02-4.00 (m, 4H), 3.27-3.26 (m, 7H). LCMS (ESI): m/z=394.1 [M+H]$^+$.

Examples 13 and 14

N-[(2S)-2-(1-Hydroxy-1-methyl-ethyl)-2-methyl-6-morpholino-3H-furo[2,3-b]pyridin-5-yl]pyrazolo[1,5-a]pyrimidine-3-carboxamide and N-[(2R)-2-(1-Hydroxy-1-methyl-ethyl)-2-methyl-6-morpholino-3H-furo[2,3-b]pyridin-5-yl]pyrazolo[1,5-a]pyrimidine-3-carboxamide

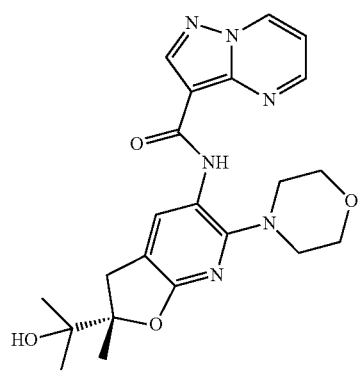

-continued

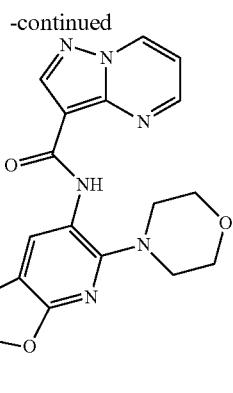

Step A. 2-(6-Fluoro-2-methyl-3H-furo[2,3-b]pyridin-2-yl)propan-2-ol

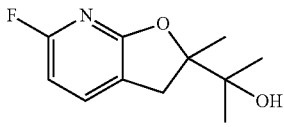

A solution of ethyl 6-fluoro-2-methyl-3H-furo[2,3-b]pyridine-2-carboxylate (500 mg, 2.22 mmol) in dry tetrahydrofuran (5 ml) was purged with nitrogen (3×) and cooled to −70° C. Methyl magnesium bromide (3M, 0.74 ml, 2.22 mmol) was added slowly and the mixture was warmed slowly to 10° C. and stirred for 16 h at 10° C. The mixture was quenched with saturated ammonium chloride solution (5 ml) and extracted with ethyl acetate (15 ml×3). The combined organic phases were washed with brine (10 ml), dried over sodium sulfate, concentrated and purified by silica gel column (eluting gradient 20-30% ethyl acetate: petroleum ether) to afford 2-(6-fluoro-2-methyl-3H-furo[2,3-b]pyridin-2-yl)propan-2-ol (380 mg, 81% yield) as a light yellow oil. $^1$H NMR (400 MHz, CDCl$_3$) δ 7.50 (t, J=7.2 Hz, 1H), 6.40 (d, J=8.0 Hz, 1H), 3.52 (d, J=15.6 Hz, 1H), 2.78 (d, J=15.6 Hz, 1H), 1.93 (s, 1H), 1.46 (s, 3H), 1.40 (s, 3H), 1.26 (s, 3H). LCMS (ESI): m/z=211.9 [M+H]$^+$.

Step B. 2-(2-Methyl-6-morpholino-3H-furo[2,3-b]pyridin-2-yl)propan-2-ol

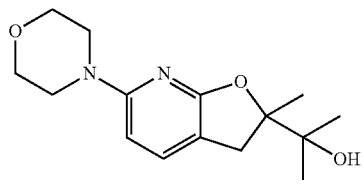 [SMILES: CC(C)(O)C1(C)Cc2ccc(N3CCOCC3)nc2O1]

2-(6-Fluoro-2-methyl-3H-furo[2,3-b]pyridin-2-yl)propan-2-ol (500 mg, 2.37 mmol) in morpholine (4.2 ml, 47.85 mmol) was heated at 120° C. for 16 h, concentrated and purified by silica gel column (eluent 30% ethyl acetate: petroleum ether) to afford 2-(2-methyl-6-morpholino-3H-furo[2,3-b]pyridin-2-yl)propan-2-ol (500 mg, 76% yield) as a light yellow oil. $^1$H NMR (400 MHz, CDCl$_3$) δ 7.31 (d, J=8.4 Hz, 1H), 6.11 (d, J=8.0 Hz, 1H), 3.80 (t, J=4.8 Hz, 4H), 3.49-3.42 (m, 5H), 2.69 (d, J=15.6 Hz, 1H), 2.05 (s, 1H), 1.43 (s, 3H), 1.38 (s, 3H), 1.24 (s, 3H). LCMS (ESI): m/z=278.9 [M+H]$^+$.

Step C. 2-(2-Methyl-6-morpholino-5-nitro-3H-furo[2,3-b]pyridin-2-yl)propan-2-ol

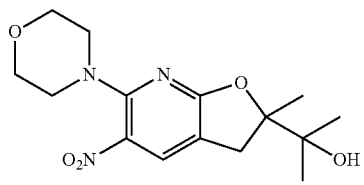 [SMILES: CC(C)(O)C1(C)Cc2cc([N+](=O)[O-])c(N3CCOCC3)nc2O1]

To 2-(2-Methyl-6-morpholino-3H-furo[2,3-b]pyridin-2-yl)propan-2-ol (340 mg, 1.22 mmol) in acetic anhydride (4 ml) was added cupric nitrate (252 mg, 1.34 mmol). The mixture was heated at 40° C. for 5 min, diluted with water (10 ml) and extracted with ethyl acetate (30 ml×3). The combined organic phases were washed with saturated sodium bicarbonate (5 ml×2) and brine (5 ml×2), dried over sodium sulfate, concentrated and purified by silica gel column (eluent 40% ethyl acetate: petroleum ether) to afford 2-(2-methyl-6-morpholino-5-nitro-3H-furo[2,3-b]pyridin-2-yl)propan-2-ol (90 mg, 23% yield) as a yellow solid. $^1$H NMR (400 MHz, CDCl$_3$) δ 8.12 (s, 1H), 3.82-3.79 (m, 4H), 3.46-3.44 (m, 5H), 2.75 (d, J=16.0 Hz, 1H), 1.49 (s, 3H), 1.41 (s, 3H), 1.27 (s, 3H). LCMS (ESI): m/z=323.9 [M+H]$^+$.

Step D. 2-(5-Amino-2-methyl-6-morpholino-3H-furo[2,3-b]pyridin-2-yl)propan-2-ol

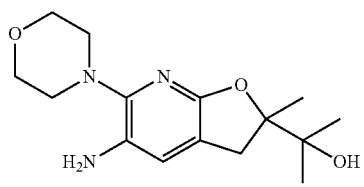 [SMILES: CC(C)(O)C1(C)Cc2cc(N)c(N3CCOCC3)nc2O1]

To 2-(2-methyl-6-morpholino-5-nitro-3H-furo[2,3-b]pyridin-2-yl)propan-2-ol (90 mg, 0.28 mmol) in ethyl acetate (5 ml) was added 10% palladium on carbon (296 mg, 0.28 mmol). The mixture was hydrogenated (15 psi) at 15° C. for 2 h, filtered and the filtrate was concentrated. The residue was purified by silica gel column (eluent 5% methanol:dichloromethane) to afford 2-(5-amino-2-methyl-6-morpholino-3H-furo[2,3-b]pyridin-2-yl)propan-2-ol (63 mg, 78% yield) as a yellow oil. $^1$H NMR (400 MHz, CDCl$_3$) δ 6.92 (s, 1H), 3.84 (t, J=4.4 Hz, 4H), 3.46 (d, J=16.0 Hz, 1H), 3.09 (t, J=4.8 Hz, 4H), 2.67 (d, J=16.0 Hz, 1H), 1.70 (br s, 3H), 1.41 (s, 3H), 1.38 (s, 3H), 1.23 (s, 3H).

Step E. N-[2-(1-Hydroxy-1-methyl-ethyl)-2-methyl-6-morpholino-3H-furo[2,3-b]pyridin-5-yl]pyrazolo[1,5-a]pyrimidine-3-carboxamide

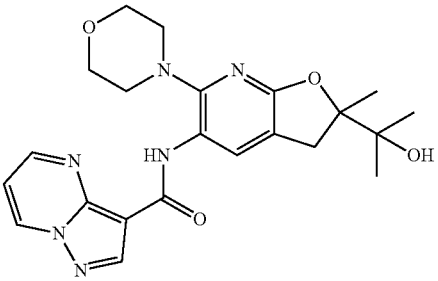 [SMILES: CC(C)(O)C1(C)Cc2cc(NC(=O)c3cnn4cccnc34)c(N3CCOCC3)nc2O1]

To 2-(5-Amino-2-methyl-6-morpholino-3H-furo[2,3-b]pyridin-2-yl)propan-2-ol (90 mg, 0.31 mmol) in pyridine (3 ml) was added pyrazolo[1,5-a]pyrimidine-3-carbonyl chloride (62 mg, 0.34 mmol). The mixture was stirred at 15° C. for 2 h, concentrated and purified by silica gel column (eluent 5% methanol:dichloromethane) to afford N-[2-(1-hydroxy-1-methyl-ethyl)-2-methyl-6-morpholino-3H-furo[2,3-b]pyridin-5-yl]pyrazolo[1,5-a]pyrimidine-3-carboxamide (80 mg, 60% yield) as a yellow oil.

Step F. N-[(2S)-2-(1-hydroxy-1-methyl-ethyl)-2-methyl-6-morpholino-3H-furo[2,3-b]pyridin-5-yl]pyrazolo[1,5-a]pyrimidine-3-carboxamide and N-[(2R)-2-(1-hydroxy-1-methyl-ethyl)-2-methyl-6-morpholino-3H-furo[2,3-b]pyridin-5-yl]pyrazolo[1,5-a]pyrimidine-3-carboxamide

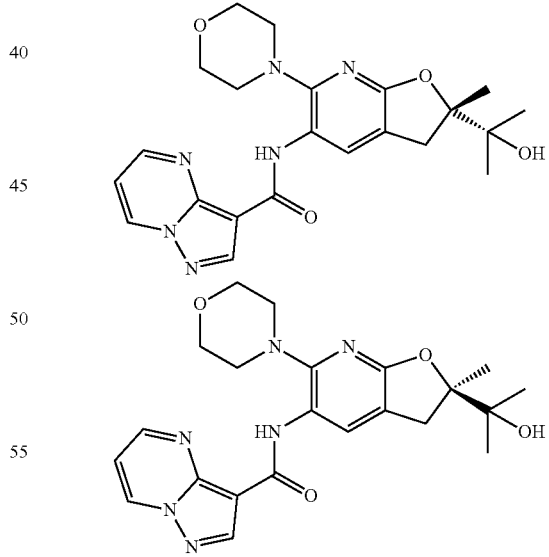

N-[2-(1-hydroxy-1-methyl-ethyl)-2-methyl-6-morpholino-3H-furo[2,3-b]pyridin-5-yl]pyrazolo[1,5-a]pyrimidine-3-carboxamide (80 mg, 0.18 mmol) was resolved by chiral SFC (AD, 250 mm*30 mm, 5 um, supercritical CO$_2$/0.1% ammonium hydroxide in ethanol=60/40, 60 ml/min) to afford N-[(2S)-2-(1-hydroxy-1-methyl-ethyl)-2-methyl-6-morpholino-3H-furo[2,3-b]pyridin-5-yl]pyrazolo

[1,5-a]pyrimidine-3-carboxamide (30 mg, 37% yield, RT=6.01 min) and N-[(2R)-2-(1-hydroxy-1-methyl-ethyl)-2-methyl-6-morpholino-3H-furo[2,3-b]pyridin-5-yl]pyrazolo[1,5-a]pyrimidine-3-carboxamide (30 mg, 37% yield, RT=6.57 min) as yellow solids. Stereochemistry was arbitrarily assigned based on peak elution.

Example 13

Peak 1: $^1$H NMR (400 MHz, CDCl$_3$) δ 10.09 (s, 1H), 8.86 (dd, J=7.2, 1.6 Hz, 1H), 8.79-8.78 (m, 2H), 8.66 (s, 1H), 7.09 (dd, J=6.8, 4.0 Hz, 1H), 3.93 (t, J=4.4 Hz, 4H), 3.54 (d, J=16.0 Hz, 1H), 3.13 (t, J=4.4 Hz, 4H), 2.80 (d, J=16.0 Hz, 1H), 2.09 (br s, 1H), 1.46 (s, 3H), 1.40 (s, 3H), 1.26 (s, 3H). LCMS (ESI): m/z=439.0 [M+H]$^+$.

Example 14

Peak 2: $^1$H NMR (400 MHz, CDCl$_3$) δ 10.09 (s, 1H), 8.86 (dd, J=6.8 Hz, 1.6 Hz, 1H), 8.79-8.78 (m, 2H), 8.66 (s, 1H), 7.09 (dd, J=6.8, 4.4 Hz, 1H), 3.93 (t, J=4.4 Hz, 4H), 3.54 (d, J=15.6 Hz, 1H), 3.13 (t, J=4.4 Hz, 4H), 2.80 (d, J=15.6 Hz, 1H), 2.08 (s, 1H), 1.46 (s, 3H), 1.40 (s, 3H), 1.26 (s, 3H). LCMS (ESI): m/z=439.0 [M+H]$^+$.

Examples 15 and 16

(S)—N-(6-(4-(2-Amino-2-oxoethyl)piperazin-1-yl)-2-(hydroxymethyl)-2-methyl-2,3-dihydrofuro[2,3-b]pyridin-5-yl)-6-methylpyrazolo[1,5-a]pyrimidine-3-carboxamide and (R)—N-(6-(4-(2-Amino-2-oxoethyl)piperazin-1-yl)-2-(hydroxymethyl)-2-methyl-2,3-dihydrofuro[2,3-b]pyridin-5-yl)-6-methylpyrazolo[1,5-a]pyrimidine-3-carboxamide

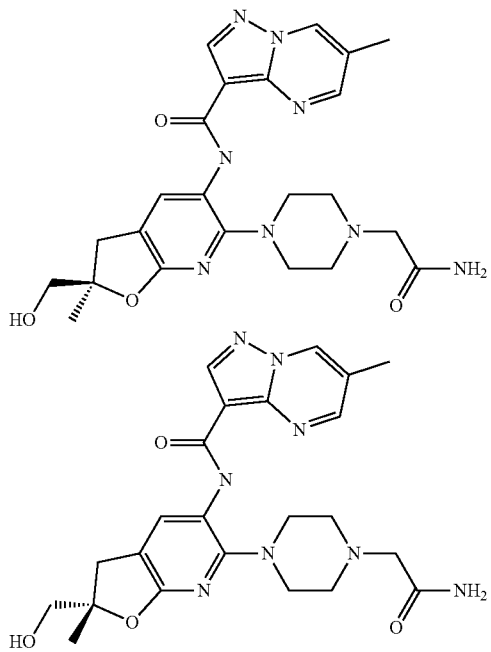

The title compound was made in a manner analogous to Examples 12 and 13 to give (S)—N-(6-(4-(2-amino-2-oxoethyl)piperazin-1-yl)-2-(hydroxymethyl)-2-methyl-2,3-dihydrofuro[2,3-b]pyridin-5-yl)-6-methylpyrazolo[1,5-a]pyrimidine-3-carboxamide (76.8 mg, 40% yield, Rt=2.49 min) and (R)—N-(6-(4-(2-amino-2-oxoethyl)piperazin-1-yl)-2-(hydroxymethyl)-2-methyl-2,3-dihydrofuro[2,3-b]pyridin-5-yl)-6-methylpyrazolo[1,5-a]pyrimidine-3-carboxamide (69.9 mg, 37% yield, Rt=3.17 min) with absolute stereochemistry assigned arbitrarily.

Example 15

Peak 1: $^1$H NMR (400 MHz, DMSO-d$_6$) δ 9.99 (s, 1H), 9.24 (s, 1H), 8.88 (d, J=1.6 Hz, 1H), 8.60 (s, 1H), 8.51 (s, 1H), 7.23 (s, 1H), 7.13 (s, 1H), 5.14 (br s, 1H), 3.49-3.40 (m, 2H), 3.21 (d, J=16.8 Hz, 1H), 3.00-2.96 (m, 6H), 2.86 (d, J=16.4 Hz, 1H), 2.70-2.69 (m, 4H), 2.45 (s, 3H), 1.35 (s, 3H). LCMS (ESI): m/z=481.1 [M+H]$^+$.

Example 16

Peak 2: $^1$H NMR (400 MHz, DMSO-d$_6$) 9.99 (s, 1H), 9.24 (s, 1H), 8.88 (d, J=2.0 Hz, 1H), 8.60 (s, 1H), 8.51 (s, 1H), 7.23 (s, 1H), 7.13 (s, 1H), 5.15 (br s, 1H), 3.49-3.40 (m, 2H), 3.22 (d, J=16.8 Hz, 1H), 3.00-2.96 (m, 6H), 2.86 (d, J=16.4 Hz, 1H), 2.70-2.69 (m, 4H), 2.45 (s, 3H), 1.35 (s, 3H). LCMS (ESI): m/z=481.1 [M+H]$^+$.

Enzymatic Assays

Compounds were assayed for inhibition of human IRAK4 and IRAK1 catalytic activity using recombinant enzyme produced from insect cells. Full-length IRAK4 protein, carrying an N-terminal His6-Tag, was obtained from Life Technologies (Carlsbad, Calif., USA). The IRAK1 construct was produced internally and was comprised of IRAK1 residues Arg194 to Ser712, preceded by an NH2-terminal His6 tag and the coding sequence for glutathione-S-transferase.

Kinase activities were assayed using the Transcreener-Fluorecescence polarization platform (BelBrook Labs, Madison, Wis., USA) that measures amounts of the reaction product, ADP. The IRAK4 reaction conditions were optimized using an IRAK1-derived peptide (sequence H-KKARFSRFAGSSPSQSSMVAR) to provide a linear reaction rate over the course of a 90 min incubation, which resulted in 10-12% conversion of the starting ATP to ADP. Final IRAK4 assay conditions were 1.25 nM IRAK4; 125 uM ATP; 10 uM MgC$_2$; 125 uM peptide in reaction buffer (25 mM HEPES (pH7.4); 2 mM Dithiothreitol; 0.015% Brij-35; and 0.5% dimethyl sulfoxide. The IRAK1 activity was optimized similarly, yielding final assay conditions of 3 mM IRAK1; 62.5 uM ATP; 5 uM MgCl$_2$, and 62.5 uM IRAK1 peptide in reaction buffer for 60 min.

Assays of compounds for kinase inhibition were performed using inhibitors serially-diluted in dimethyl sulfoxide, which was accomplished with a LabCyte Echo 555 liquid dispenser. 384 well assay plates spotted with compound received 4 ul of a 2× substrate (ATP+peptide) mix in reaction buffer, followed by 4 ul of 2× enzyme diluted in reaction buffer. Reactions were halted at 60 (IRAK1) or 90 (IRAK4) min by addition of 6 ul of detection buffer, containing EDTA (40 nM final concentration), 0.95 ug of the ADP-binding antibody ADP2, ADP tracer (3 nM final concentration), and 25 uM HEPES. Following a 1 hr incubation, fluorescence polarization of the ADP2-antibody::TRACER complex was read on a Tecan M1000 plate reader using a 635/20 excitation filter in combination with a 670/20 emission filter. Delta milli-P values were analyzed using Genedata software to fit dose-response curves and compute compound Ki values, using ATP Km values of 642 um and 83.2 uM for IRAK4 and IRAK1, respectively. Table 3 provides IRAK4 Ki values for representative compounds of the present invention.

TABLE 3

IRAK4 Ki values of representative compounds of the present invention.

| Ex. | IRAK4 Ki (uM) |
|---|---|
| 1 | 0.039 |
| 2 | 0.0042 |
| 3 | 0.0041 |
| 4 | 0.033 |
| 5 | 0.0056 |
| 6 | 0.004 |
| 7 | 2.4 |
| 8 | 0.82 |
| 9 | 0.0076 |
| 10 | 0.088 |
| 11 | 0.045 |
| 12 | 0.54 |
| 13 | 0.091 |
| 14 | 0.048 |
| 15 | 0.0066 |
| 16 | 0.0055 |
| 17 | 0.0064 |
| 18 | 0.21 |
| 19 | 0.031 |
| 20 | 0.0091 |
| 21 | 0.013 |

Kinetic Solubility Assay

Kinetic solubility of IRAK4 inhibitors described herein may be improved (that is, raised in value) compared to matched pairs according to the following substructures and depicted in FIG. 1:

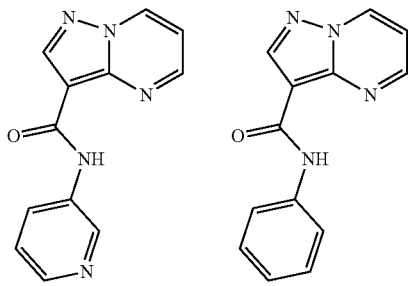 [SMILES: O=C(Nc1cccnc1)c1cnn2cccnc12 ; O=C(Nc1ccccc1)c1cnn2cccnc12]

The kinetic solubility assay started with compound DMSO stock solutions. This assay used Millipore Multiscreen 96-well filter plates for the 24 hour equilibration shaking. Samples were prepared by adding 4 µL of the 10 mM compound DMSO stock solutions into 196 µL of PBS buffer pH 7.4 in the 96-well filter plates, yielding a compound concentration of 200 µM and 2% DMSO. The filter plate was sealed with aluminum sealing film and shaken at room temperature for 24 hours at 1000 rpm. When shaking has completed, the solutions were filtered into a clean 96-well plate utilizing a vacuum manifold. After filtration, some precipitate is often observed at the bottom of the filtration plate wells. Most of the precipitates appear to be crystalline under a polarizing light microscope. The filtrate samples were diluted by a factor of 2 using PBS pH7.4 buffer and then transferred to a 384-well plate for analysis by UHPLC-CLND (CLND: Chemiluminescence nitrogen detector). 5 µL of each sample was injected twice into the UHPLC-CLND for two repeat analysis.

Data Processing and Solubility Determination

Samples were detected and analyzed using UV 254 nm and CLND. UV 254 nm is used primarily to confirm the sample purity but in rare cases, is also used to quantify the concentration of compounds with no nitrogens, where additional work is done to create a compound specific calibration curve. The identification of CLND target peaks of each compound were confirmed by LCMS. Sample quantification was accomplished by CLND peak intensity, the calibration curve, and the number of nitrogen contained in the compound. One calibration curve of caffeine was used for solubility quantitative determination. A fresh calibration curve was created for every batch. The number of nitrogens in a compound used for this quantification was corrected for the actual configuration of the nitrogen in the compound.

TABLE 4

Kinetic solubilities of representative compounds of the present invention and their matched pairs.

| Ex. | Kinetic solubility (µM) | Kinetic solubility of matched pair phenyl compound (µM) | Fold improvement in kinetic solubility |
|---|---|---|---|
| 3 | 7.5 | 1 | 7.5 |
| 19 | 177 | 5.6 | 31.6 |
| 12 | 39 | 6.9 | 5.7 |
| 18 | 167 | 13 | 12.8 |
| 9 | 137 | 1 | 137.0 |
| 6 | 143 | 9.8 | 14.6 |
| 21 | 124 | 4.6 | 27.0 |
| 5 | 112 | 2.6 | 43.1 |
| 10 | 159 | 10 | 15.9 |
| 11 | 137 | 10 | 13.7 |
| 1 | 166 | 1 | 166.0 |

Plasma Protein Binding Using Rapid Equilibrium Dialysis (RED)

Figure 2:
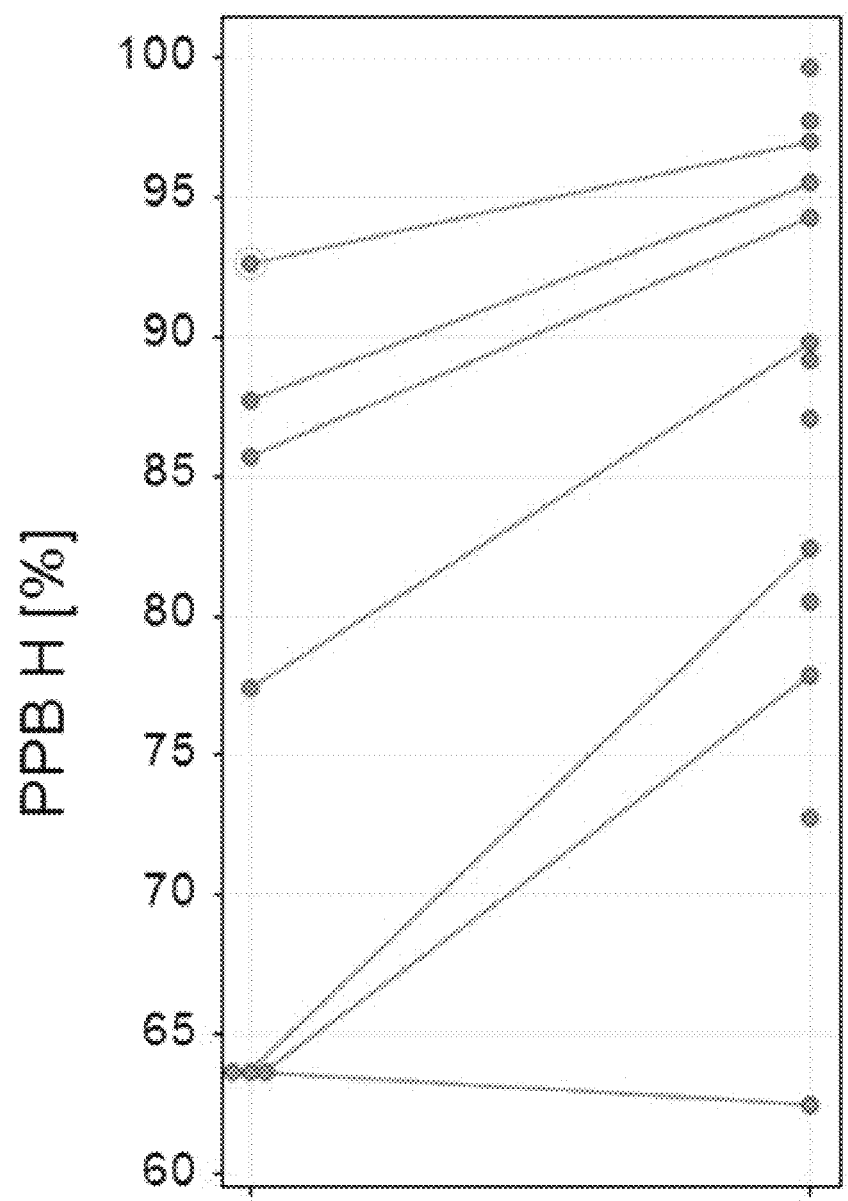
FIG. 2 illustrates a matched pair analysis regarding plasma protein binding values of certain compounds of the present invention having a particular substructure (points on the right) and corresponding compounds of a different substructure, wherein a single aromatic ring carbon (points on the right) is replaced with N (points on the left).

Plasma protein binding (PPB) of IRAK4 inhibitors described herein may be improved (that is, lowered in value) compared to matched pairs according to the following substructures and depicted in FIG. 2:

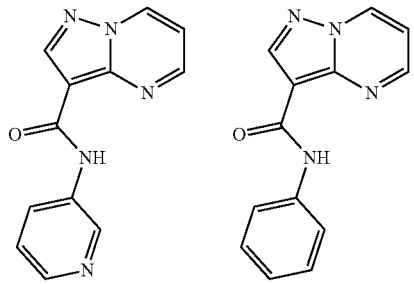 [SMILES: O=C(Nc1cccnc1)c1cnn2cccnc12 ; O=C(Nc1ccccc1)c1cnn2cccnc12]

Plasma protein binding was measured in duplicate using rapid equilibrium dialysis (RED) device ((Thermo Scientific Pierce) in a 96-well format. Briefly, 10.0 µL drug or control compounds (0.5 mM in DMSO) was mixed with 1000 µL plasma (pH adjusted to 7.4) from various species (BioreclamationIVT). Aliquots of 300 µL drug/plasma mixture were placed into the donor side chamber of a single-use RED plate, and 500 µL aliquots of PBS buffer were placed into the adjacent chamber as the receiver side. The plate was incubated on an orbital shaker at 400 rpm, at 37° C. for 4 hours. After completion of incubation, 50 μL aliquots from the PBS buffer side were mixed with 5 μL of blank plasma matrix, and 5 μL from the donor side (plasma) were mixed with 50 μL blank PBS buffer. All samples were then crashed with 200 μL acetonitrile (containing internal standard) to precipitate plasma proteins. The samples were centrifuged at 3750 rpm for 10 min to pellet the proteins. The supernatants were carefully transferred to a fresh 96-well plate, and diluted with an equivalent volume of water. The samples were then analyzed by LC-MS/MS (ABI 4000, ABI Sciex). Data acquisition and processing was performed with Analyst 1.6.1 and Multiquant 2.1. The percent of protein binding and fraction unbound (fu) in matrix was calculated from taking the ratio of responses (peak areas) on the receiver side (buffer) to those on the donor side (plasma). The ratios were normalized to the internal standard.

TABLE 5

Plasma protein binding values of representative compounds of the present invention and their matched pairs.

| Ex. | Human PPB (%) | Human PPB of of matched pair phenyl compound (%) |
|---|---|---|
| 2 | 92.6 | 97 |
| 6 | 77.4 | 89.8 |
| 9 | 87.7 | 95.5 |
| 21 | 63.7 | 82.4 |
| 1 | 85.7 | 94.3 |

What is claimed is:

1. A compound of Formula I

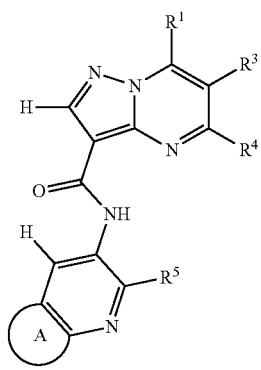

(I)

or a stereoisomer or pharmaceutically acceptable salt thereof,
wherein:
  $R^1$ is hydrogen or halo;
  $R^3$ is hydrogen, halo, CN, OH, $C_{1-3}$alkyl, $C_{2-3}$alkenyl, $C_{3-7}$cycloalkyl, $C_1$-$C_3$alkanoyl, —($C_0$-$C_3$alkyl)C(O)NR$^6$R$^7$, —NR$^8$R$^9$, a 3-7 membered monocyclic saturated or partially saturated heterocyclic ring, a 5-6 membered monocyclic heteroaryl ring, or a 5-6 membered monocyclic aryl ring,
    wherein any alkyl, alkanoyl, or alkenyl is independently optionally substituted by halo, oxo, CN, OH, $C_{1-3}$alkoxy, or $C_{1-3}$haloalkoxy, and any cycloalkyl or other ring is independently optionally substituted by halo, oxo, CN, OH, $C_{1-3}$alkyl, or $C_{1-3}$haloalkyl;
  $R^4$ is hydrogen, halo, $C_{1-3}$alkyl, $C_{2-3}$alkenyl, —($C_0$-$C_3$alkyl)C(O)R$^{13}$, —($C_{0-3}$alkyl)C(O)NR$^{10}$R$^{11}$, or —NR$^8$R$^9$,
    wherein any alkyl or alkenyl is independently optionally substituted by halo, oxo, CN, OH, $C_{1-3}$alkoxy, or $C_{1-3}$haloalkoxy;
  $R^5$ is $C_{1-6}$alkyl, $C_{1-6}$alkoxy, $C_{3-10}$cycloalkyl, a 3-11 membered saturated or partially saturated heterocyclic ring, or a 5-6 membered monocyclic heteroaryl ring, wherein any alkoxy is independently optionally substituted by halo, OH, $C_{3-7}$cycloalkyl, $C_{1-3}$alkoxy, or $C_{1-3}$haloalkoxy, and
    any cycloalkyl or other ring is optionally substituted by halo, oxo, CN, OH, —($C_{0-3}$alkyl)C(O)NR$^{10}$R$^{11}$, or $C_{1-3}$alkyl optionally substituted by halo, oxo, CN, OH, or —NR$^8$R$^9$;
  A is a 3-11 membered heterocyclic ring optionally substituted by halo, oxo, CN, OH, $C_{1-6}$ alkyl, or $C_{3-6}$cycloalkyl,
    wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
  $R^6$ and $R^7$ are, independently at each occurrence, hydrogen, $C_{1-3}$ alkyl, or $C_{3-6}$cycloalkyl,
    wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
  $R^8$, $R^9$, $R^{10}$ and $R^{11}$ are, independently at each occurrence, hydrogen, $C_{1-6}$alkyl, $C_{3-6}$cycloalkyl, a 3-11 membered saturated heterocyclic ring, —C(O)R$^{13}$, —C(O)OR$^{13}$, or —C(O)NR$^6$R$^7$,
    wherein any alkyl, cycloalkyl or other ring is independently optionally substituted by halo, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;
  $R^{12}$ is, independently at each occurrence, hydrogen, $C_{1-6}$alkyl or $C_{3-6}$cycloalkyl,
    wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy; and
  $R^{13}$ is, independently at each occurrence, hydrogen, $C_{1-6}$alkyl, $C_{3-10}$cycloalkyl, or a 3-11 membered saturated heterocyclic ring,
    wherein any alkyl, cycloalkyl, or other ring is independently optionally substituted by halo, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$.

2. The compound of claim 1, further defined as a compound of Formula (II):

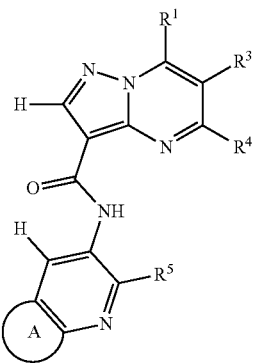

(II)

or a stereoisomer or pharmaceutically acceptable salt thereof,
wherein:
$R^1$ is hydrogen or halo;
$R^3$ is hydrogen, halo, CN, OH, $C_{1-3}$alkyl, $C_{2-3}$alkenyl, $C_{3-7}$cycloalkyl, $C_1$-$C_3$alkanoyl, —($C_0$-$C_3$alkyl)C(O)NR$^6$R$^7$, —NR$^8$R$^9$, a 3-7 membered monocyclic saturated or partially saturated heterocyclic ring, a 5-6 membered monocyclic heteroaryl ring, or a 5-6 membered monocyclic aryl ring,
  wherein any alkyl, alkanoyl, or alkenyl is independently optionally substituted by halo, oxo, CN, OH, $C_{1-3}$ alkoxy, or $C_{1-3}$haloalkoxy, and any cycloalkyl or other ring is independently optionally substituted by halo, oxo, CN, OH, $C_{1-3}$alkyl, or $C_{1-3}$haloalkyl;
$R^4$ is hydrogen, halo, $C_{1-3}$alkyl, $C_{2-3}$ alkenyl, —($C_{0-3}$alkyl)C(O)NR$^{10}$R$^{11}$, or —($C_0$-$C_3$alkyl)C(O)R$^{13}$,
  wherein any alkyl or alkenyl is independently optionally substituted by halo, oxo, CN, OH, $C_{1-3}$alkoxy, or $C_{1-3}$haloalkoxy;
$R^5$ is $C_{1-6}$alkyl, $C_{1-6}$alkoxy, $C_{3-10}$cycloalkyl, a 3-11 membered saturated or partially saturated heterocyclic ring, or a 5-6 membered monocyclic heteroaryl ring, wherein any alkoxy is independently optionally substituted by halo, OH, $C_{3-7}$cycloalkyl, $C_{1-3}$alkoxy, or $C_{1-3}$haloalkoxy, and
  any cycloalkyl or other ring is optionally substituted by halo, oxo, CN, OH, —($C_{0-3}$alkyl)C(O)NR$^{10}$R$^{11}$, or $C_{1-3}$ alkyl optionally substituted by halo, oxo, CN, OH, or —NR$^8$R$^9$;
A is a 3-11 membered heterocyclic ring optionally substituted by halo, oxo, CN, OH, $C_{1-6}$ alkyl, or $C_{3-6}$cycloalkyl,
  wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
$R^6$ and $R^7$ are, independently at each occurrence, hydrogen, $C_{1-3}$ alkyl, or $C_{3-6}$cycloalkyl,
  wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;
$R^8$, $R^9$, $R^{10}$ and $R^{11}$ are, independently at each occurrence, hydrogen, $C_{1-6}$alkyl, $C_{3-6}$cycloalkyl, a 3-11 membered saturated heterocyclic ring, —C(O)R$^{13}$, —C(O)OR$^{13}$, or —C(O)NR$^6$R$^7$,
  wherein any alkyl, cycloalkyl or other ring is independently optionally substituted by halo, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;
$R^{12}$ is, independently at each occurrence, hydrogen, $C_{1-6}$alkyl or $C_{3-6}$cycloalkyl,
  wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy; and
$R^{13}$ is, independently at each occurrence, hydrogen, $C_{1-6}$alkyl, $C_{3-10}$cycloalkyl, or a 3-11 membered saturated heterocyclic ring,
  wherein any alkyl, cycloalkyl, or other ring is independently optionally substituted by halo, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$.

3. The compound of claim 1, or a stereoisomer or pharmaceutically acceptable salt thereof, wherein $R^1$ and $R^4$ are each hydrogen, and $R^3$ is hydrogen, halo, $CH_3$, $CH_2F$, $CHF_2$, $CF_3$, cyclopropyl, or —C(O)CH$_3$.

4. The compound of claim 1, or a stereoisomer or pharmaceutically acceptable salt thereof, wherein $R^1$ and $R^4$ are each hydrogen, and $R^3$ is hydrogen or $CH_3$.

5. The compound of claim 1, or a stereoisomer or pharmaceutically acceptable salt thereof, wherein $R^1$, $R^3$ and $R^4$ are each hydrogen.

6. The compound of claim 1, or a stereoisomer or pharmaceutically acceptable salt thereof, wherein $R^5$ is a 3-11 membered saturated or partially saturated heterocyclic ring optionally substituted by halo, oxo, CN, OH, —($C_{0-3}$alkyl)C(O)NR$^{10}$R$^{11}$, or $C_{1-3}$alkyl optionally substituted by halo, oxo, CN, OH, or —NR$^8$R$^9$.

7. The compound of claim 1, or a stereoisomer or pharmaceutically acceptable salt thereof, wherein $R^5$ is an N-linked 3-7 membered saturated heterocyclic ring optionally substituted by halo, oxo, CN, OH, —($C_{0-3}$alkyl)C(O)NR$^{10}$R$_{11}$, or $C_{1-3}$ alkyl optionally substituted by halo, oxo, CN, OH, or —NR$^8$R$^9$.

8. The compound of claim 1, or a stereoisomer or pharmaceutically acceptable salt thereof, wherein the ring heteroatoms of the 3-11 membered saturated or partially saturated heterocyclic ring of $R^5$ are selected from nitrogen and oxygen.

9. The compound of claim 1, or a stereoisomer or pharmaceutically acceptable salt thereof, wherein $R^5$ is N-linked piperidinyl, N-linked piperazinyl, or N-linked morpholinyl, wherein any $R^5$ is optionally substituted by halo, oxo, CN, OH, or $C_{1-3}$ alkyl optionally substituted by halo, oxo, CN, or OH.

10. The compound of claim 1, or a stereoisomer or pharmaceutically acceptable salt thereof, wherein the following portion of Formula I,

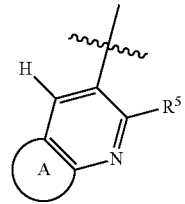

is further defined as I-A:

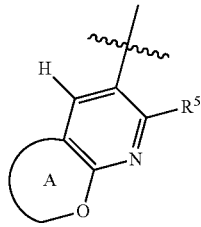
(I-A)

wherein A is a 5 or 6 membered ring optionally containing an additional ring nitrogen and wherein A is optionally substituted by halo, oxo, CN, OH, $C_{1-6}$ alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy.

11. The compound of claim 10, or a stereoisomer or pharmaceutically acceptable salt thereof, wherein I-A is further defined as I-B:

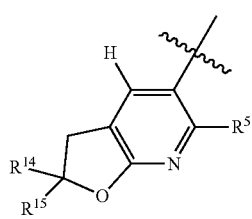
(I-B)

wherein $R^{14}$ and $R^{15}$ are each selected from halo, oxo, CN, OH, $C_{1-6}$ alkyl and $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy;

or $R^{14}$ and $R^{15}$ together form a $C_{3-6}$cycloalkyl or saturated or partially saturated 3-6 membered heterocyclic ring, wherein any cycloalkyl or other ring is independently optionally substituted by halo, oxo, CN, OH, $C_{1-3}$alkyl, $C_{1-3}$haloalkyl, $C_{1-3}$alkoxy, or $C_{1-3}$haloalkoxy.

12. The compound of claim 11, wherein $R^{14}$ and $R^{15}$ are each selected from halo, oxo, CN, OH, $C_{1-6}$ alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy.

13. The compound of claim 1, or a stereoisomer or pharmaceutically acceptable salt thereof, wherein A is a 3-11 membered heterocyclic ring comprising only one oxygen as a ring atom and is optionally substituted by (i) OH or (ii) $C_{1-6}$alkyl optionally substituted by OH.

14. The compound of claim 1, or a stereoisomer or pharmaceutically acceptable salt thereof, wherein the following portion of Formula I,

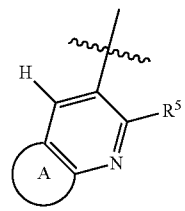

is further defined as I-C:

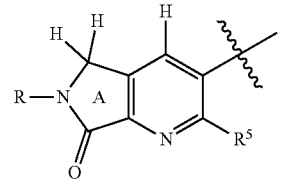
(I-C)

wherein R is $C_{1-6}$alkyl or $C_{3-6}$cycloalkyl, wherein any alkyl or cycloalkyl is independently optionally substituted by halo, oxo, CN, OH, $C_{1-3}$alkyl, $C_{1-3}$haloalkyl, $C_{1-3}$alkoxy, or $C_{1-3}$haloalkoxy.

15. The compound of claim 1, wherein the compound is not

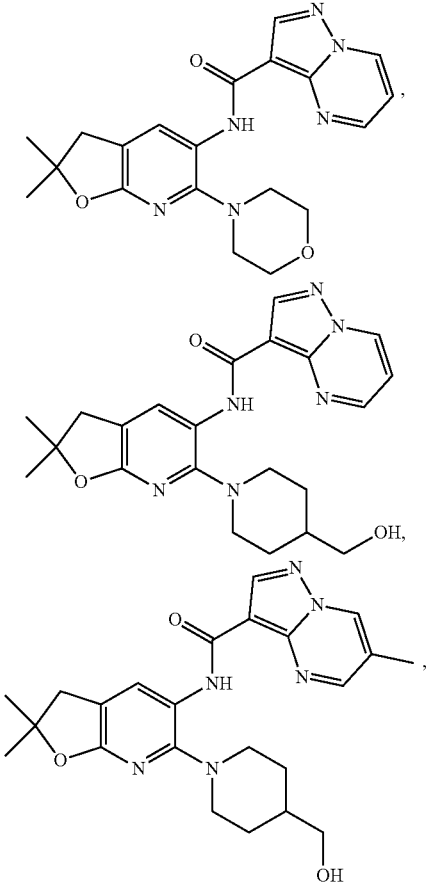

81
-continued
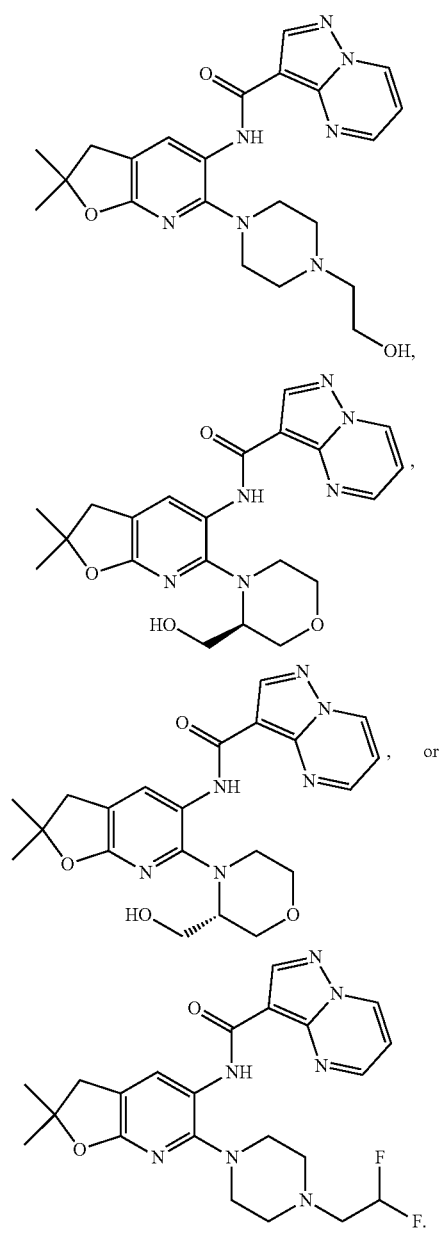
16. The compound of claim 1, wherein the compound is selected from:
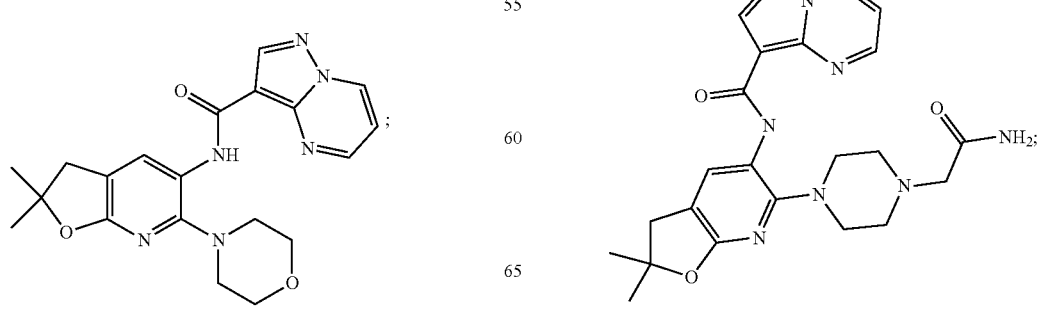
82
-continued
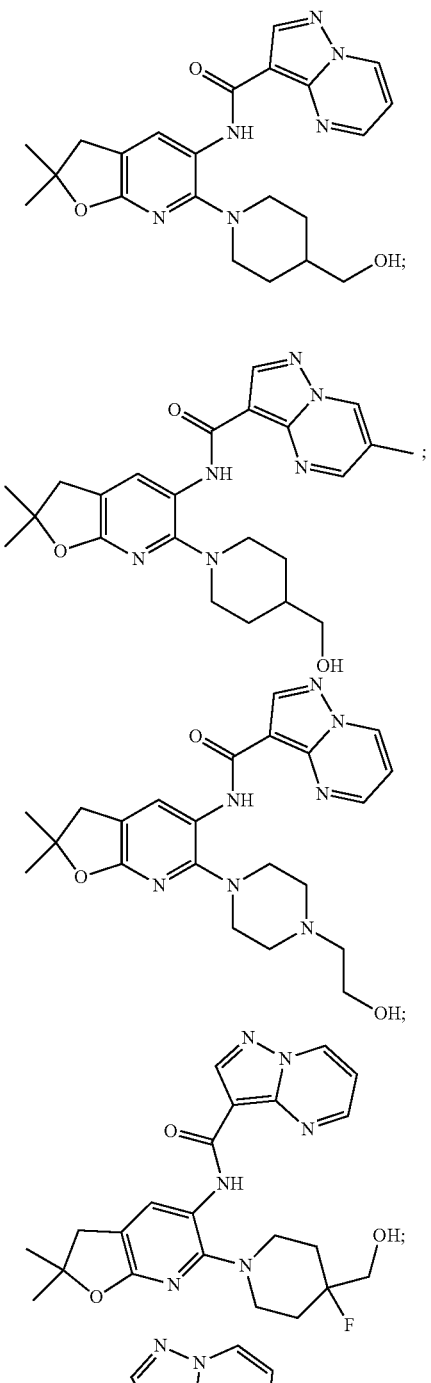

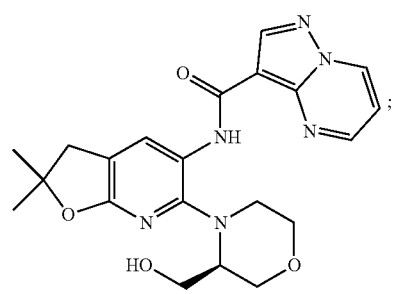
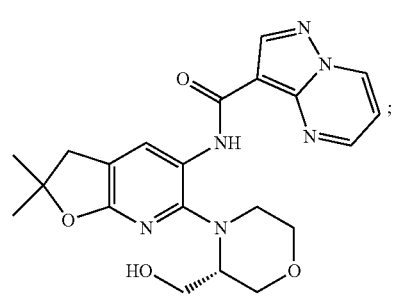
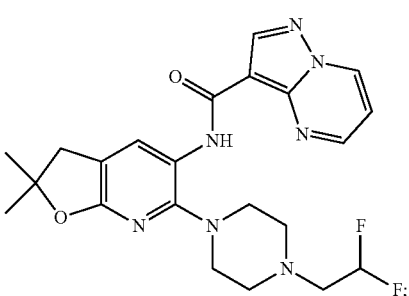
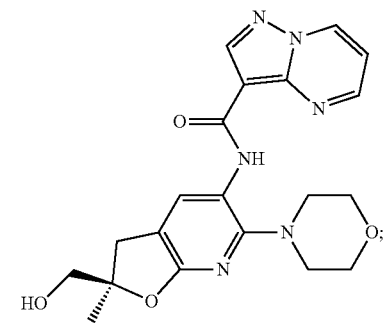
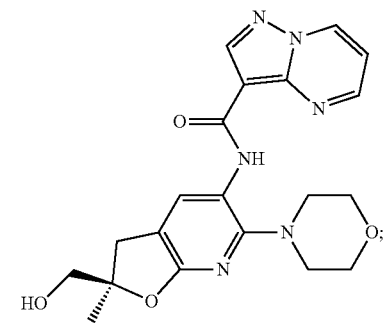
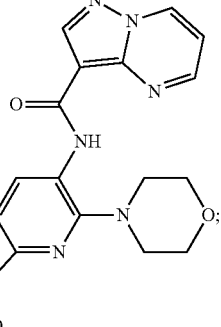
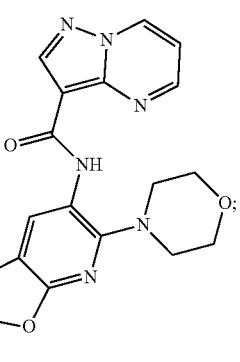
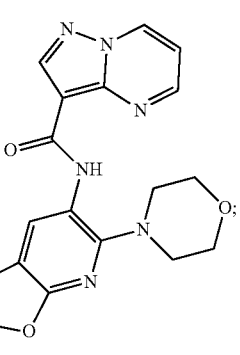
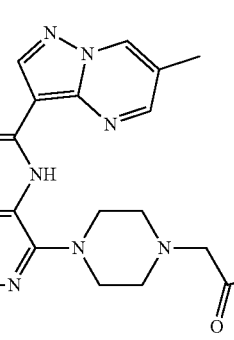
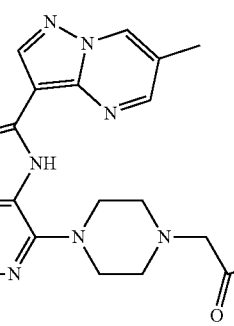

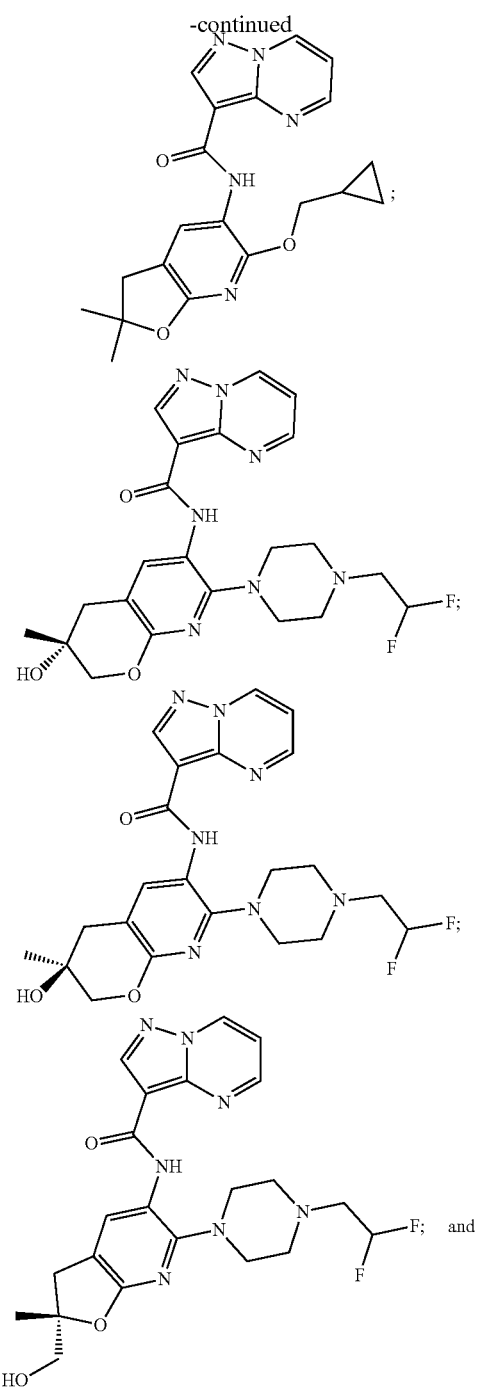

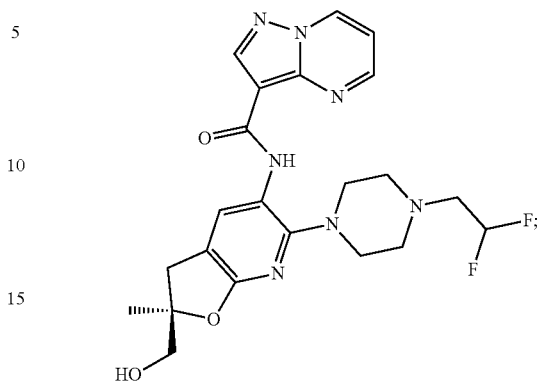

or a stereoisomer or pharmaceutically acceptable salt thereof.

17. A pharmaceutical composition comprising a compound of claim 1, or a stereoisomer or pharmaceutically acceptable salt thereof, and a pharmaceutically acceptable excipient, carrier or diluent.

18. A method of treating, or lessening the severity of a disease or condition responsive to the inhibition of IRAK4 in a patient, comprising administering to the patient a therapeutically effective amount of a compound of claim 1, or a stereoisomer or pharmaceutically acceptable salt thereof.

19. A method for treating cancer in a patient wherein the cancer is leukemia, lymphoid or myeloid malignancy, comprising administering to the patient a therapeutically effective amount of a compound of claim 1, or a stereoisomer or pharmaceutically acceptable salt thereof.

20. A method for treating an inflammatory or autoimmune disease in a patient wherein the disease is selected from asthma, rhinitis, allergic airway syndrome, atopic dermatitis, bronchitis, rheumatoid arthritis, psoriasis, lupus, chronic obstructive pulmonary disease (COPD), contact dermatitis, chronic obstructive pulmonary disease and delayed hypersensitivity reactions, comprising administering to the patient a therapeutically effective amount of a compound of claim 1, or a stereoisomer or pharmaceutically acceptable salt thereof.

* * * * *